United States Patent
Bollu et al.

(10) Patent No.: US 11,318,116 B2
(45) Date of Patent: May 3, 2022

(54) STABLE AMORPHOUS FORM OF SACUBITRIL VALSARTAN TRISODIUM COMPLEX AND PROCESSES FOR PREPARATION THEREOF

(71) Applicant: Laurus Labs Limited, Hyderabad (IN)

(72) Inventors: Ravindra Babu Bollu, Hyderabad (IN); Ram Thaimattam, Hyderabad (IN); Venkateswar Rao Challagonda, Hyderabad (IN); Sivarami Reddy Yasam, Hyderabad (IN); Pavan Kumar Seethamraju, Hyderabad (IN); Uma Maheswar Rao Vasireddi, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 17/028,495

(22) Filed: Sep. 22, 2020

(65) Prior Publication Data

US 2021/0046050 A1 Feb. 18, 2021

Related U.S. Application Data

(62) Division of application No. 16/340,907, filed as application No. PCT/IB2017/056255 on Oct. 10, 2017, now Pat. No. 10,857,132.

(30) Foreign Application Priority Data

Oct. 10, 2016 (IN) .............................. 201641034689

(51) Int. Cl.
| | | |
|---|---|---|
| C07C 233/47 | (2006.01) | |
| A61K 31/41 | (2006.01) | |
| A61K 31/197 | (2006.01) | |
| A61K 47/32 | (2006.01) | |
| A61K 47/38 | (2006.01) | |
| A61K 31/216 | (2006.01) | |
| C07D 257/04 | (2006.01) | |

(52) U.S. Cl.
CPC ............ *A61K 31/41* (2013.01); *A61K 31/197* (2013.01); *A61K 31/216* (2013.01); *A61K 47/32* (2013.01); *A61K 47/38* (2013.01); *C07C 233/47* (2013.01); *C07D 257/04* (2013.01); *C07B 2200/13* (2013.01)

(58) Field of Classification Search
CPC .................................................. C07C 233/47
See application file for complete search history.

(56) References Cited

U.S. PATENT DOCUMENTS 5,217,996 A 6/1993 Ksander
8,877,938 B2 11/2014 Feng et al.

FOREIGN PATENT DOCUMENTS

| CN | 104860894 A | 8/2015 | |
|---|---|---|---|
| CN | 105037289 A | 11/2015 | |
| CN | 105348209 A | 2/2016 | |
| CN | 105461647 A | 4/2016 | |
| CN | 105622535 A | 6/2016 | |
| CN | 106316973 A | 1/2017 | |
| CN | 106518709 A | 3/2017 | |
| IN | 3835/DEL/2015 | 5/2017 | |
| IN | 4304/DEL/2015 | 6/2017 | |
| WO | WO-2016125123 A1 | 8/2001 | |
| WO | WO-2007056546 A1 | 5/2007 | |
| WO | WO 2016/037552 A1 | 3/2016 | |
| WO | WO-2016/049663 A1 | 3/2016 | |
| WO | WO-2016/051393 A2 | 4/2016 | |
| WO | WO-2016074651 A * | 5/2016 | ........... C07C 211/35 |
| WO | WO-2016/151525 A1 | 9/2016 | |
| WO | WO-2016135751 A1 | 9/2016 | |
| WO | WO-2016/201238 A1 | 12/2016 | |
| WO | WO-2017/009784 A1 | 1/2017 | |
| WO | WO-2017/012917 A1 | 1/2017 | |
| WO | WO-2017/036420 A1 | 3/2017 | |
| WO | WO-2017/037591 A1 | 3/2017 | |
| WO | WO-2017/037596 A1 | 3/2017 | |
| WO | WO-2017/042700 A1 | 3/2017 | |
| WO | WO-2017/085573 A1 | 5/2017 | |
| WO | WO-2017/097085 A1 | 6/2017 | |
| WO | WO-2017/097275 A1 | 6/2017 | |
| WO | WO-2017/154017 A1 | 9/2017 | |

OTHER PUBLICATIONS

International Search Report for PCT/IB2017/056255 dated Feb. 2-16, 2018 (5 pages).

* cited by examiner

*Primary Examiner* — Shawquia Jackson
(74) *Attorney, Agent, or Firm* — Blank Rome LLP

(57) ABSTRACT

The present invention relates to stable amorphous form of sacubitril valsartan trisodium complex and its solid dispersion compounds, processes for their preparation and pharmaceutical composition comprising the same. The present invention also relates to an improved process for the preparation of sacubitril sodium and its use in the preparation of sacubitril valsartan trisodium complex.

14 Claims, 12 Drawing Sheets

STABLE AMORPHOUS FORM OF SACUBITRIL VALSARTAN TRISODIUM COMPLEX AND PROCESSES FOR PREPARATION THEREOF

CROSS-REFERENCE TO RELATED APPLICATIONS

This application is a divisional application that is based on and claims the benefit of the filing data and disclosure of U.S. patent application Ser. No. 16/340,907, filed Apr. 10, 2019, which is a national stage application of and claims the benefit of the filing date and disclosure of International Application PCT/IB2017/056255, filed Oct. 10, 2017, which is based on and claims the benefit of the filing date and disclosure under Indian Provisional Application No. 201641034689, filed on Oct. 10, 2016, entitled "Process for preparation of amorphous form of sacubitril valsartan trisodium complex", the content of each of which are incorporated by reference herein.

FIELD OF THE INVENTION

The present invention generally relates to stable amorphous form of sacubitril valsartan trisodium complex, processes for their preparation and pharmaceutical composition comprising the same.

The present invention further provides amorphous solid dispersion of sacubitril valsartan trisodium complex, processes for their preparation and pharmaceutical composition comprising the same.

The present invention also provides an improved process for the preparation of sacubitril sodium salt and its use in the preparation of sacubitril valsartan trisodium complex.

BACKGROUND OF THE INVENTION

Sacubitril together with valsartan, known as LCZ696, is a complex comprised of anionic forms of sacubitril and valsartan, sodium cations and water molecules in the molar ratio of 1:1:3:2.5, respectively, and which is represented by a compound of Formula I:

A complex comprising valsartan, which is an angiotension receptor antagonist, and Sacubitril, which is a neprilysin inhibitor, has been approved by US Food and Drug Administration (FDA) under the trade name ENTRESTO® by Novartis for the treatment of heart failure with reduced ejection fraction.

Entresto is a first-in-class medicine (an Angiotensin Receptor Neprilysin Inhibitor, or ARM) and has a unique mode of action which is thought to reduce the strain on the failing heart. It harnesses the body's natural defenses against heart failure, simultaneously acting to enhance the levels of natriuretic and other endogenous vasoactive peptides, while also inhibiting the renin-angiotensin-aldosterone system (RAAS).

U.S. Pat. No. 8,877,938 ("the '938 patent") disclosed a complex of trisodium sacubitril valsartan hemipentahydrate in crystalline form and process for preparation thereof. The '938 patent process involves preparation of complex of trisodium sacubitril valsartan hemipentahydrate by dissolving sacubitril free acid and valsartan free acid in acetone, combined the resulting solution with aqueous sodium hydroxide and the obtained solution was evaporated to yield trisodium sacubitril valsartan as a glassy solid. The glassy solid residue is then treated with acetone and sonicated to obtain crystalline trisodium sacubitril valsartan hemipentahydrate. The glassy solid resulted in the '938 patent is not well characterized and does not disclose any polymorphic information. On repetition of the '938 patent process, the present inventors have found that glassy solid of trisodium sacubitril valsartan was obtained as an amorphous form and the same was characterized by XRD pattern.

Chinese patent publication No. 105461647 ("the '647 publication") disclosed crystalline Form A of Sacubitril valsartan trisodium. The '647 publication further disclosed an amorphous Form α, Form β and Form γ of Sacubitril valsartan trisodium and their preparation by dissolving sacubitril and valsartan in a solvent such as ethanol, treating with aqueous sodium base followed by addition of resulting reaction mixture to an anti-solvent to obtain amorphous Form α, Form β and Form γ of sacubitril valsartan trisodium

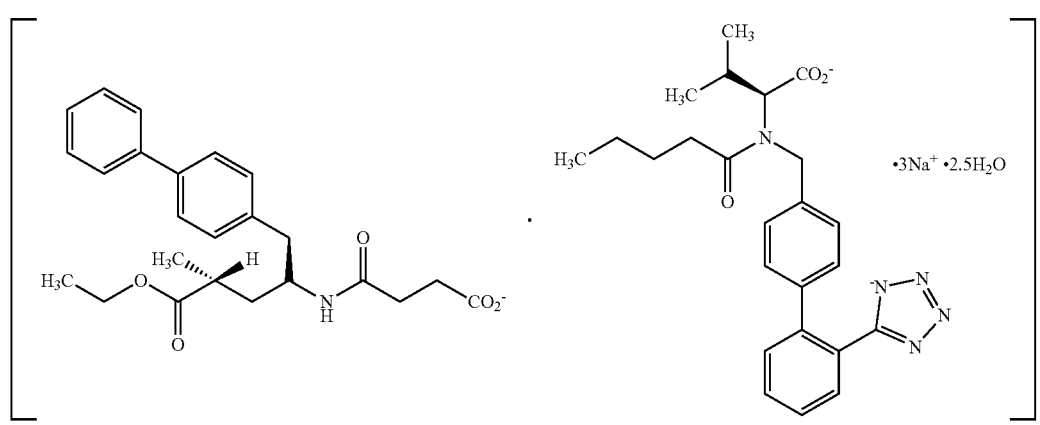

Formula I

Chemically, valsartan is known as (S)-3-methyl-2-(N-{[2'-(2H-1,2,3,4-tetrazol-5-yl)biphenyl-4-yl]methyl}pentanamido)butanoic acid and sacubitril is known as 4-{[(2S,4R)-1-(4-biphenylyl)-5-ethoxy-4-methyl-5-oxo-2-pentanyl] amino}-4-oxo-butanoic acid.

complex. The '647 publication also disclosed another preparation method for preparation of amorphous Form γ of sacubitril valsartan trisodium by dissolving sacubitril, valsartan and aqueous sodium base in ethanol and concentrating the reaction mixture to obtain amorphous Form γ.

PCT Publication No. 2016/125123 ("the '123 publication") disclosed amorphous trisodium sacubitril valsartan. The amorphous form has been prepared by different processes by either dissolving trisodium sacubitril valsartan hemipentahydrate in a solvent or in a mixture of solvents followed by isolation or by dissolving sacubitril and valsartan in a solvent followed addition of sodium source, removal of the solvent, optionally treating the resulting reaction mass with mixture of solvents and isolating of amorphous trisodium sacubitril valsartan. The '123 publication also disclosed another preparation method for preparation of amorphous trisodium sacubitril valsartan by dissolving trisodium sacubitril valsartan in a polar solvent, adding the resulting solution to a non-polar solvent and finally isolating amorphous form.

Chinese patent publication Nos. 104860894 ("the '894 publication"), 105348209 (the '209 publication") and 105622535 ("the 535 publication") disclosed a method for the preparation of complex of trisodium sacubitril valsartan by addition of aqueous sodium hydroxide to the reaction mixture containing sacubitril and valsartan.

PCT Publication No. 2017/009784 ("the 784 publication") disclosed an amorphous form of trisodium salt of valsartan sacubitril complex and its preparation method by treating sacubitril sodium salt and valsartan disodium or sacubitril and valsartan in the presence of a sodium ion source in one or more solvents followed by removal of solvent. However, this patent publication neither disclosed the impurities formed nor disclosed the control of impurities.

PCT Publication No. 2017/012917 ("the 917 publication") disclosed an amorphous powder comprising a 1:1 stoichiometric mixture of the trisodium salts of Valsartan and Sacubitril and having a water content of at maximum 4% by weight and its preparation method by dissolving crystalline trisodium sacubitril valsartan hemipentahydrate in water or in a mixture of water and a water miscible solvent followed by freeze drying or spray drying the resulting solution to obtain amorphous form. The '917 publication also disclosed another preparation method for preparation of amorphous trisodium sacubitril valsartan by addition of sodium hydroxide to the reaction mixture containing sacubitril and valsartan followed by freeze drying or spray drying the resulting solution to obtain amorphous compound.

PCT Publication No. 2017/037596 ("the 596 publication") disclosed an amorphous solid dispersion of sacubitril valsartan trisodium complex with one or more pharmaceutically acceptable carrier and further disclosed a preparation method of amorphous form of trisodium sacubitril valsartan by dissolving trisodium sacubitril valsartan complex in methanol or in a mixture of methanol and acetone followed by evaporation of the solvent by rotavapor.

PCT Publication No. 2017/037591 ("the '591 publication") disclosed a process for the preparation of amorphous form of sacubitril valsartan sodium complex by reacting sacubitril with valsartan in a solvent followed addition of sodium source, removal of the solvent, treating with an organic solvent and removing the solvent and then finally isolating the amorphous form of sacubitril valsartan sodium complex. The '591 publication further disclosed that the amorphous form of Sacubitril Valsartan sodium salt obtained from this process is stable at 25±2° C./30±5% RH.

Chinese patent publication No. 106316973 ("the '973 publication") disclosed amorphous trisodium sacubitril valsartan and its process.

PCT Publication No. 2017/042700 ("the '700 publication") disclosed an amorphous solid salt form comprising valsartan and sacubitril and its preparation method by treating valsartan and sacubitril with a source of cation in a solvent.

Chinese patent publication No. 106518709 ("the '709 publication") disclosed a process for the preparation of amorphous Sacubitril/Valsartan sodium by addition of sodium source to the reaction mixture containing sacubitril and valsartan followed by freeze drying or spray drying the resulting solution to obtain amorphous compound.

PCT Publication No. 2017036420 ("the '420 publication") disclosed an amorphous solid dispersion of sacubitril valsartan complex with one or more pharmaceutically acceptable carrier.

PCT Publication No. 2017/085573 ("the 573 publication") disclosed an amorphous solid dispersion of sacubitril valsartan trisodium complex with one or more pharmaceutically acceptable carrier and further disclosed amorphous sacubitril-valsartan complex and its preparation method by addition of sodium hydroxide to the reaction mixture containing sacubitril and valsartan followed by removal of solvent.

PCT Publication No. 2017/154017 ("the '017 publication") disclosed various methods for the preparation of amorphous form of trisodium salt of valsartan sacubitril by dissolving sacubitril sodium salt and valsartan disodium salts in aq methanol followed by removal of solvent or by addition of sodium hydroxide to the reaction mixture containing sacubitril and valsartan. The '017 publication also disclosed another preparation method for the preparation of amorphous form of trisodium salt of valsartan sacubitril by dissolving trisodium sacubitril valsartan complex in a solvent or in a mixture of solvents followed by removal of the solvent to obtain amorphous compound. However, this patent publication neither disclosed the impurities formed nor disclosed the control of impurities. The '017 publication disclosed amorphous solid dispersion of sacubitril valsartan complex with one or more pharmaceutically acceptable carrier.

PCT Publication No. 2017/097275 ("the '275 publication") disclosed the preparation of sacubitril sodium salt by conversion of crude sacubitril free acid to the crystalline amines salts, neutralizing the sacubitril amine salts with acid and isolating crystalline sacubitril free acid from an organic solvent. Finally, the crystalline sacubitril free acid thus formed is further converted to its sacubitril sodium salt. According to this publication, the conversion of crude sacubitril free acid to the crystalline amine salts leads to removal of impurities which were formed during the synthesis of sacubitril free acid, especially the lactone impurity. This process requires additional steps such as formation of sacubitril amine salt, conversion of the sacubitril amine salt to pure crystalline sacubitril free acid, isolation of the crystalline sacubitril free acid and its conversion to sacubitril sodium, which are tedious, labour intensive and time consuming thereby not viable for commercial scale operations.

Several other polymorphic forms of complex of sacubitril valsartan have been reported in the art such as:

Chinese patent publication No. 105037289 ("the '289 publication") disclosed crystalline Form II of a complex of sacubitril valsartan.

PCT Publication No. 2016/037552 ("the '552 publication") disclosed crystalline sacubitril valsartan sodium hydrate such as sacubitril valsartan 3Na.2.5H$_2$O, sacubitril valsartan 3Na.3.1H$_2$O, sacubitril valsartan 18Na.18.5H$_2$O, sacubitril valsartan 3Na.2.9H$_2$O & sacubitril valsartan 18Na.17.5H$_2$O, sacubitril valsartan 3Na.6.5H$_2$O & sacubitril valsartan 3Na.3.0H$_2$O.

PCT Publication No. 2016/049663 ("the '663 publication") disclosed crystalline trisodium sacubitril-valsartan hydrate Form I, Form II & Form III.

PCT Publication No. 2016/051393 ("the '393 publication") disclosed crystalline trisodium sacubitril valsartan hydrate Form IV.

PCT Publication No. 2016/151525 ("the '525 publication") disclosed crystalline Form I of sacubitril valsartan 3Na.3.5H$_2$O.

PCT Publication No. 2016/201238 ("the '238 publication") disclosed crystalline form II of trisodium valsartan: sacubitril and amorphous trisodium valsartan: sacubitril.

PCT Publication No. 2017/009784 ("the 784 publication") disclosed crystalline Form-II, Form III and Form-IV of trisodium salt of valsartan sacubitril complex.

IN Application No. 3835/DEL/2015 ("the 3835" application) disclosed crystalline trisodium sacubitril-valsartan hemipentahydrate.

IN Application No. 4304/DEL/2015 ("the 4304" application) disclosed crystalline trisodium sacubitril-valsartan hemipentahydrate.

PCT Publication No. 2017/097085 ("the 085 publication") disclosed crystalline trisodium sacubitril-valsartan hydrate Form II.

The amorphous form of sacubitril valsartan trisodium complex disclosed is highly unstable as it was indicated to store below at room temperature at about 25-35% RH. Storage of drug products at low temperatures and low RH atmosphere are always additional burden to the cost of the product. The amorphous form of sacubitril valsartan trisodium complex prepared by the present invention is stable even at accelerated conditions and is away from the difficulties associated with the prior art methods.

The present invention provides a stable amorphous form of sacubitril valsartan trisodium complex, wherein the stable amorphous sacubitril valsartan trisodium complex does not convert to any other solid form when stored at a temperature of up to about 40° C. and at a relative humidity of about 25% to about 75% for up to about six months. The present invention further provides an amorphous solid dispersion of sacubitril valsartan trisodium complex with one or more pharmaceutically acceptable carrier.

Further, the prior-art processes for the preparation of amorphous form of sacubitril valsartan trisodium complex involves reaction of sacubitril free acid, valsartan free acid and a suitable sodium source in a solvent. However, the sacubitril free acid obtained from the known chemical processes may contaminated with impurities, which are carry forward into sacubitril valsartan trisodium complex, if untreated at the free acid stage itself. These impurities once formed in the final sacubitril valsartan trisodium complex are difficult to remove as additional purifications at final stage may disturb the linkage between the sacubitril, valsartan and trisodium. Therefore compromising the purity of the final sacubitril-valsartan complex; thus in order to improve the purity of the final sacubitril-valsartan complex it is necessary to remove these impurities from sacubitril free acid before forming the complex without compromising the yield.

In view of the drawbacks of the reported processes, the present inventors have developed improved processes for the preparation of sacubitril valsartan trisodium complex, particularly in an amorphous form which allows the final product to be produced in a higher yield and purity which is very practical for scale-up production, especially in terms of operating efficiency.

The present invention provides an improved processes for preparation of sacubitril valsartan trisodium complex by removing the impurities formed during the synthesis of sacubitril by formation of sacubitril as its sodium salt and subsequent purifications, if any, prior to use in the formation of sacubitril valsartan trisodium complex, which makes the process simple, environmental-friendly, economical, industrially feasible and scalable.

SUMMARY OF THE INVENTION

The present invention encompasses a stable amorphous form of sacubitril valsartan trisodium complex with high product yield and quality, processes for their preparation a pharmaceutical composition comprising the same and amorphous solid dispersion of sacubitril valsartan trisodium complex with one or more pharmaceutically acceptable carrier and its preparation method. The present invention further provides an improved process for the preparation of sacubitril sodium salt and its use in the preparation of sacubitril valsartan trisodium complex.

In accordance with one embodiment, the present invention provides a stable amorphous form of sacubitril valsartan trisodium complex.

In accordance with one embodiment, the present invention provides a stable amorphous form of sacubitril valsartan trisodium complex, wherein the amorphous sacubitril valsartan trisodium complex does not convert to any other solid form when stored at a temperature of up to about 40° C. and at a relative humidity of about 25% to about 75% for about three months or more.

In accordance with another embodiment, the present invention provides processes for the preparation of amorphous form of sacubitril valsartan trisodium complex.

In accordance with another embodiment, the present invention provides a process for preparation of amorphous form of sacubitril valsartan trisodium complex, comprising:
  a) providing a solution or suspension of valsartan sodium and sacubitril sodium salt in a suitable solvent (S1),
  b) removing the solvent from the step a) reaction mass,
  c) optionally adding a suitable solvent (S2) to the step b); and
  d) isolating the amorphous form.

In accordance with another embodiment, the present invention provides a process for preparation of amorphous form of sacubitril valsartan trisodium complex, comprising:
  a) providing a solution or suspension of valsartan sodium and sacubitril sodium salt in a suitable solvent (S1),
  b) removing the solvent from the step a) reaction mass,
  c) optionally adding a suitable solvent (S2) to the step b); and
  d) isolating the amorphous form; wherein the suitable solvent (S1) is selected from the group consisting of ketones, alcohols, amides, sulfoxides, ethers and mixtures thereof; and the suitable solvent (S2) is selected from the group consisting of water, ethers, aliphatic hydrocarbons, alicyclic hydrocarbons and the like and mixtures thereof.

In accordance with another embodiment, the present invention provides a process for preparation of amorphous form of sacubitril valsartan trisodium complex, comprising:
  a) providing a solution or suspension of trisodium sacubitril valsartan complex in a suitable solvent (S1),
  b) removing the solvent from the step a) reaction mass, c) optionally adding a suitable solvent (S2) to the step b); and d) isolating the amorphous form.

In accordance with another embodiment, the present invention provides amorphous solid dispersion of sacubitril valsartan trisodium complex.

In accordance with another embodiment, the present invention provides amorphous solid dispersion of sacubitril valsartan trisodium complex with one or more pharmaceutically acceptable carrier; wherein the pharmaceutically acceptable carrier comprises one or more of a povidone, copovidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids.

In accordance with another embodiment, the present invention provides a process for the preparation of amorphous solid dispersion of sacubitril valsartan trisodium complex with one or more pharmaceutically acceptable carrier, which comprising:

a) providing a solution or suspension of valsartan sodium, sacubitril sodium salt and one or more pharmaceutically acceptable carrier in a suitable solvent (S3) or mixture of solvents; and b) isolating the amorphous solid dispersion; wherein the pharmaceutically acceptable carrier comprises one or more of a povidone, copovidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids; and wherein the suitable solvent (S3) is selected from the group consisting of water, alcohols and ketones and the like and mixtures thereof.

In accordance with another embodiment, the present invention provides a process for the preparation of amorphous solid dispersion of sacubitril valsartan trisodium complex with one or more pharmaceutically acceptable carrier, which comprising:

a) providing a solution or suspension of sacubitril valsartan trisodium complex and one or more pharmaceutically acceptable carrier in a suitable solvent (S3) or mixture of solvents; and b) isolating the amorphous solid dispersion; wherein the pharmaceutically acceptable carrier comprises one or more of a povidone, copovidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids.

In accordance with another embodiment, the present invention provides a process for preparation of sacubitril sodium salt of formula II,

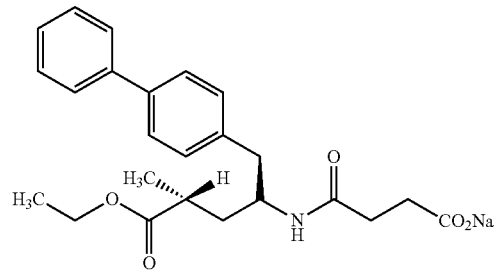

Formula II comprising:

a) reacting a compound of formula III with a suitable halogen source in the presence of ethanol and a non-polar solvent to obtain a compound of formula IV or its acid addition salt thereof;

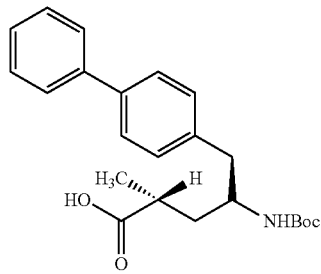

Formula III

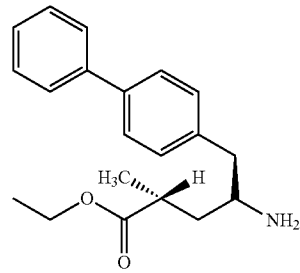

Formula IV b) treating the compound of formula IV or its acid addition salt with succinic anhydride in the presence of base to obtain sacubitril of formula V; and

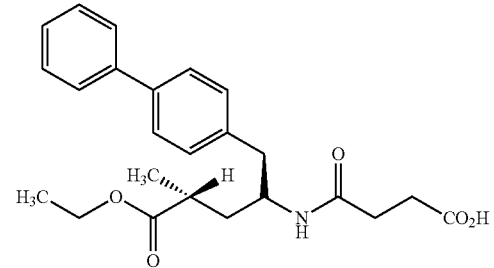

Formula V c) treating sacubitril of formula V with a suitable sodium source to obtain sacubitril sodium of formula II.

In accordance with another embodiment, the present invention provides a process for purification of sacubitril sodium salt of Formula II, comprising:
  i) dissolving sacubitril sodium salt of Formula II in one or more solvents,
  ii) optionally adding an antisolvent to the step i) reaction mixture or vice-versa, and
  iii) isolating the pure sacubitril sodium salt of Formula II; wherein the one or more solvents are selected from the group consisting of ketones, esters, halogenated hydrocarbons and the like and mixtures thereof; and the antisolvent is selected from the group consisting of ethers, aromatic hydrocarbons, aliphatic or cyclic hydrocarbons and mixtures thereof.

In another embodiment, the sacubitril sodium salt of Formula II prepared by the process of the present invention is further converted to sacubitril valsartan trisodium complex by the process as disclosed herein above.

In accordance with another embodiment, the present invention provides a process for the preparation of amorphous form of sacubitril valsartan trisodium complex, comprising:
  (a) reacting a compound of formula III with a suitable halogen source in the presence of ethanol and a non-polar solvent to obtain a compound of formula IV or its acid addition salt thereof;
  (b) treating the compound of formula IV or its acid addition salt with succinic anhydride in the presence of base to obtain sacubitril of formula V;
  (c) treating sacubitril of formula V with sodium source to obtain sacubitril sodium salt of formula II;
  (d) optionally purifying sacubitril sodium salt of formula II; and
  (e) converting sacubitril sodium salt of formula II into its amorphous form of sacubitril valsartan trisodium complex.

In another embodiment, the present invention provides sacubitril sodium having less than 0.1% of one or more of desethyl sacubitril impurity of Formula B, lactam impurity of Formula C and succinamide impurity of Formula D as measured by HPLC.

In accordance with another embodiment, the present invention provides an amorphous form of sacubitril valsartan trisodium complex having about 99.5% or more as determined by high performance liquid chromatography (HPLC).

In another embodiment, the present invention provides an amorphous form of sacubitril valsartan trisodium complex obtained by the processes as described just above having purity of about 98% or more, of about 99% or more, of about 99.5% or more and having less than 0.1% of one or more of desethyl sacubitril impurity of Formula B, lactam impurity of Formula C and succinamide impurity of Formula D as measured by high performance liquid chromatography (HPLC).

In accordance with another embodiment, the present invention provides a pharmaceutical composition comprising an amorphous form of sacubitril valsartan trisodium complex or an amorphous solid dispersion of sacubitril valsartan trisodium complex with at least one pharmaceutically acceptable carrier prepared by the processes of the present invention and optionally at least one pharmaceutically acceptable excipient.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

Figure 1:
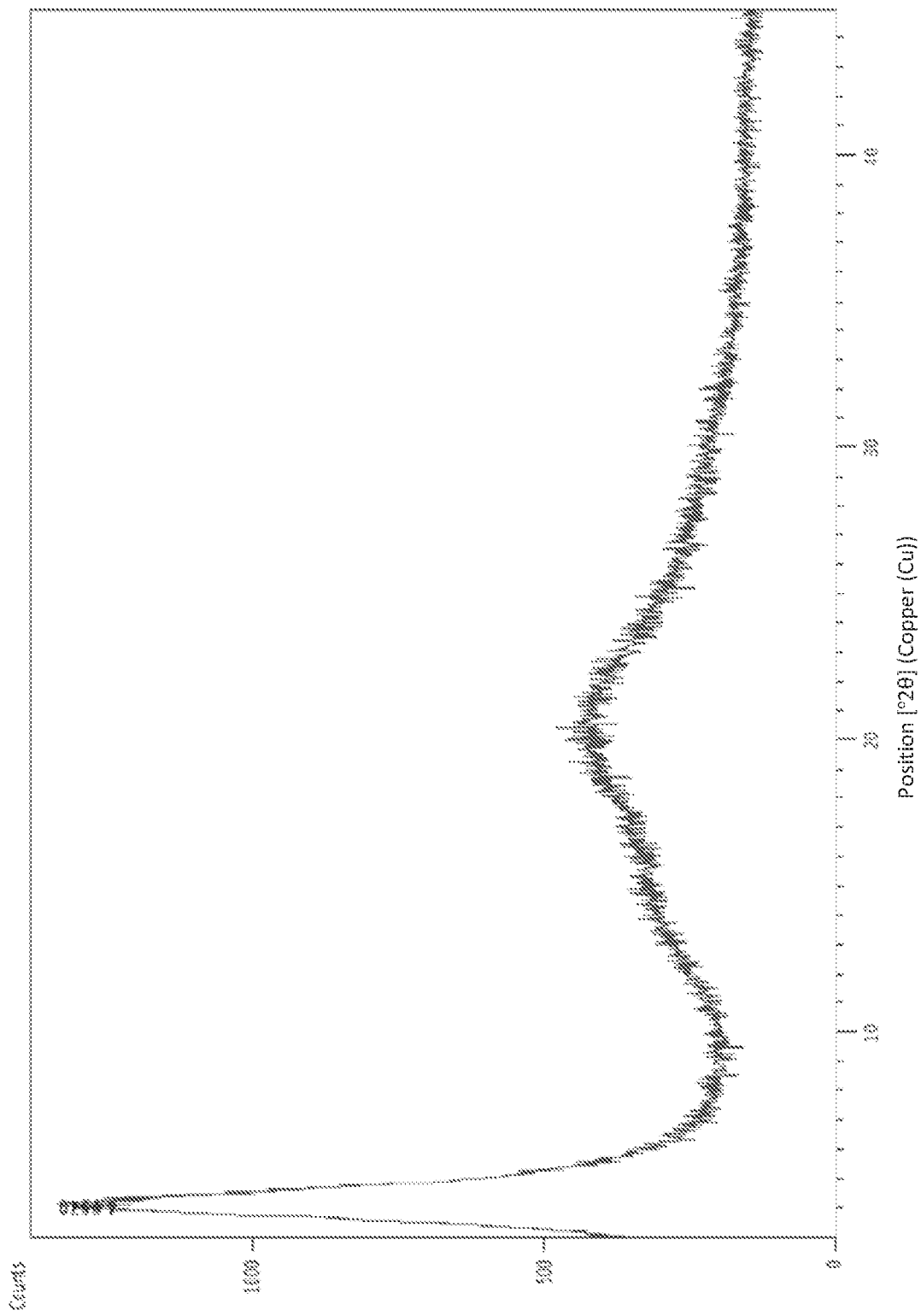
FIG. 1 is the characteristic powder X-ray diffraction (XRD) pattern of amorphous form of sacubitril valsartan trisodium complex prepared according to reference example 1.
Figure 2:
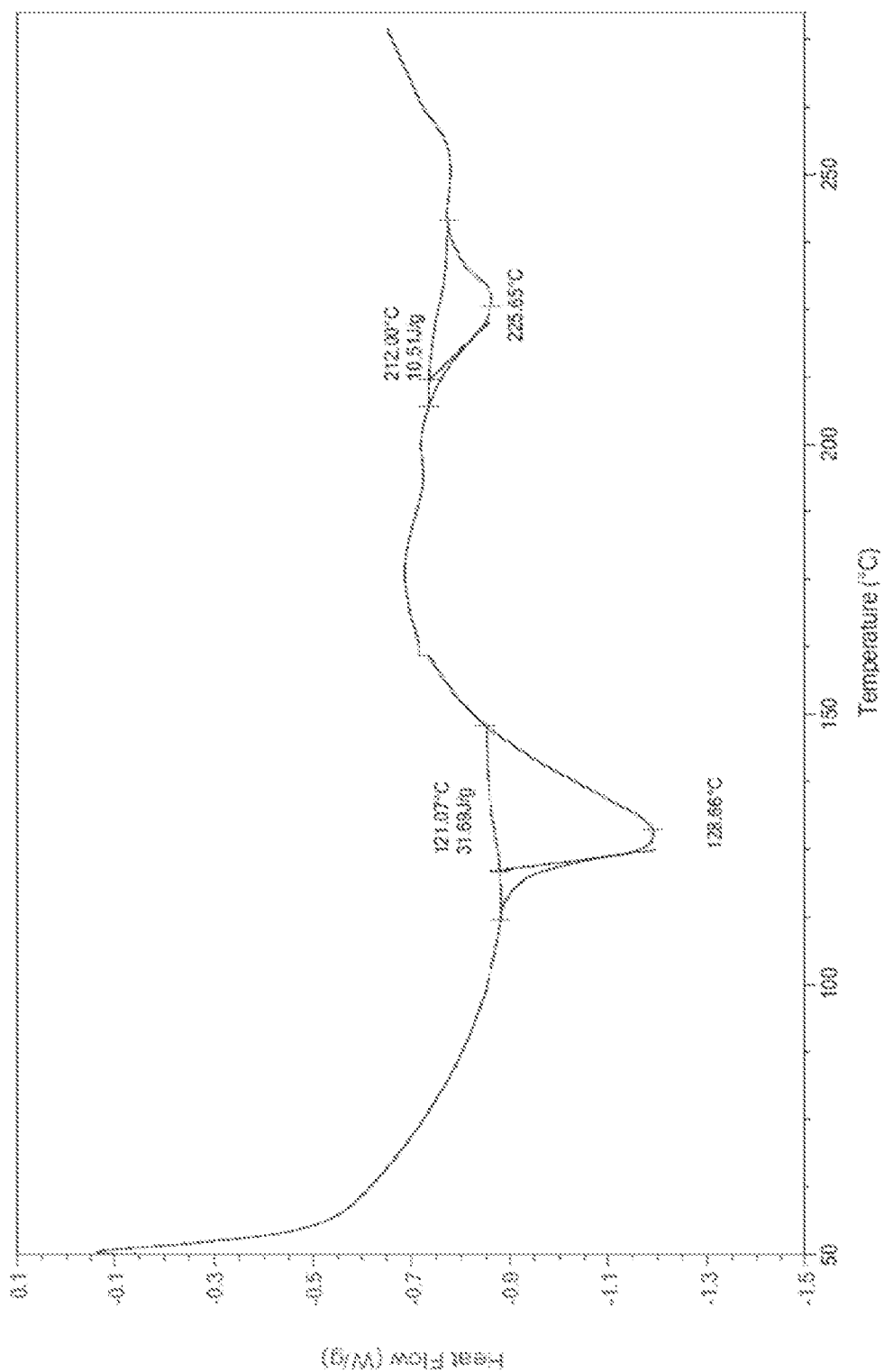
FIG. 2 is the characteristic differential scanning calorimetric (DSC) thermogram of amorphous form of sacubitril valsartan trisodium complex prepared according to reference example 1.
Figure 3:
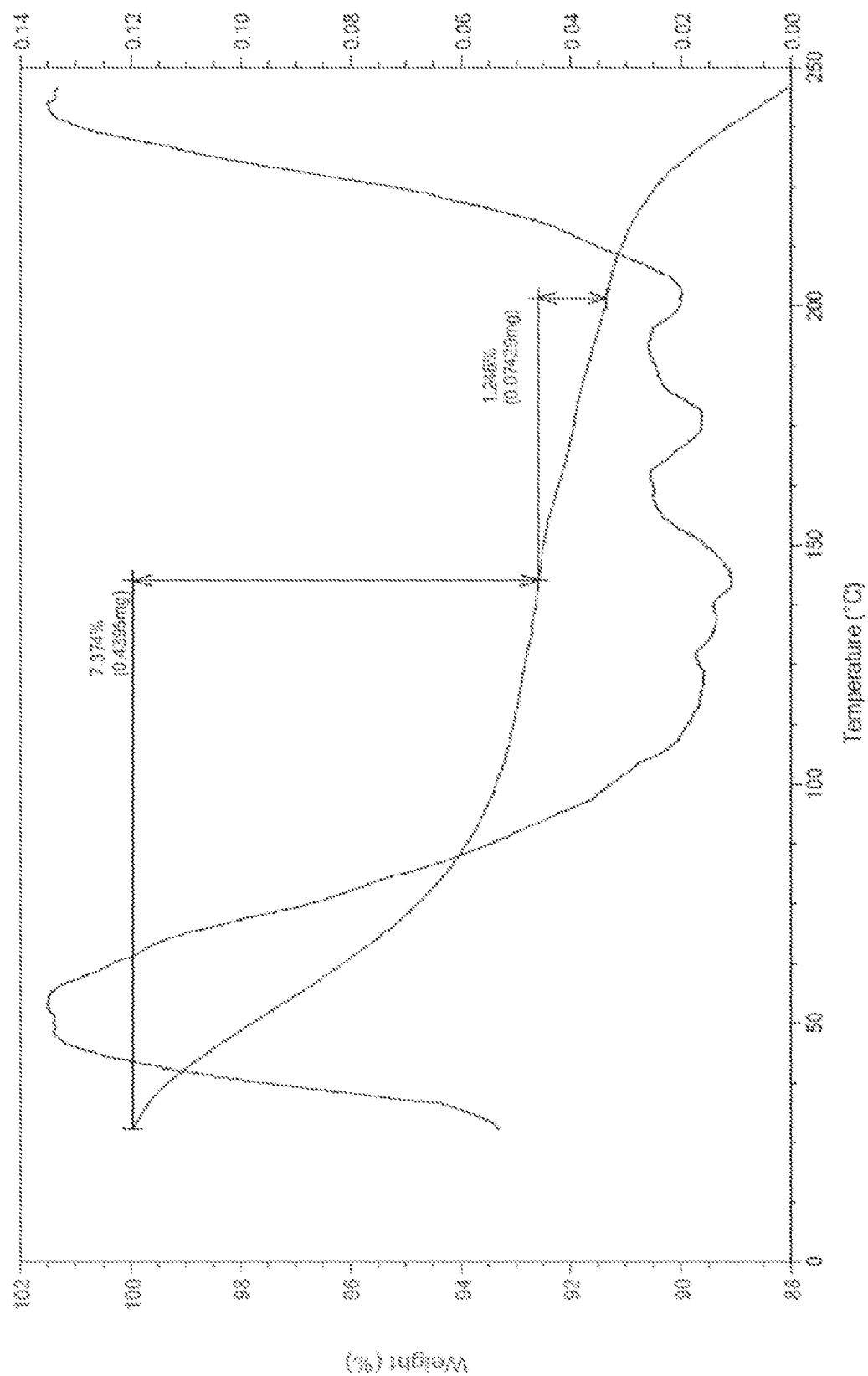
FIG. 3 is the characteristic thermo gravimetric analysis (TGA) of amorphous form of sacubitril valsartan trisodium complex prepared according to reference example 1.
Figure 4:
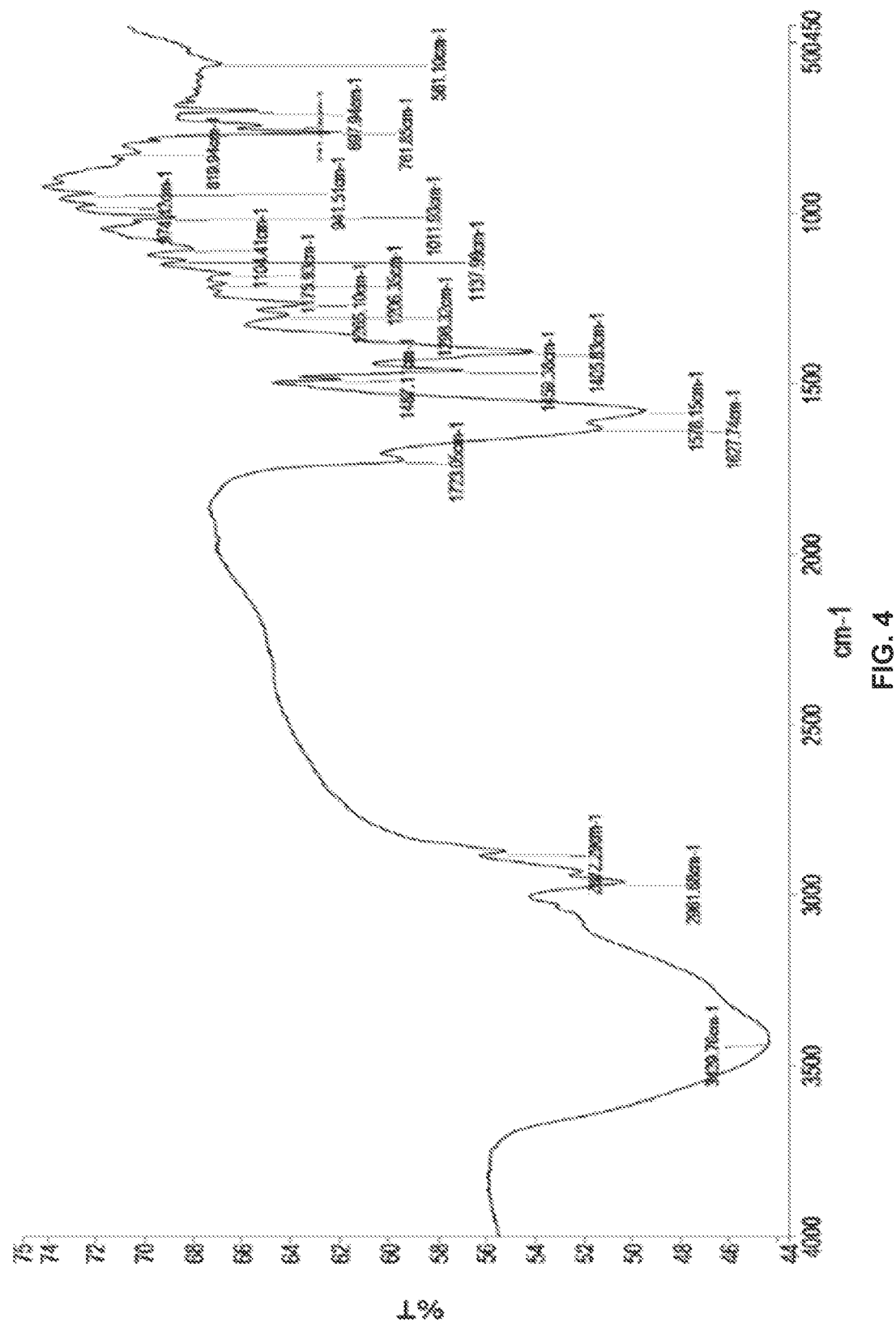
FIG. 4 is the characteristic Infrared spectroscopy (IR) of amorphous form of sacubitril valsartan trisodium complex prepared according to reference example 1.

The present invention provides a stable amorphous form of sacubitril valsartan trisodium complex with high product yield and quality, processes for its preparation, a pharmaceutical composition comprising the same and amorphous solid dispersion of sacubitril valsartan trisodium complex with one or more pharmaceutically acceptable carrier and its preparation method. The present invention further provides an improved process for the preparation of sacubitril sodium salt and its use in the preparation of sacubitril valsartan trisodium complex.

The amorphous form of sacubitril valsartan trisodium complex obtained by the process of the present invention are characterized by one or more analytical methods such as X-ray powder diffraction (XRPD) patterns, differential scanning calorimetry (DSC) curves and thermo gravimetric analysis (TGA).

As used herein, the term "solid dispersion" means any solid composition having at least two components. In certain embodiments, a solid dispersion as disclosed herein include an active ingredients dispersed among at least one other component, for example a polymer.

In one embodiment, the present invention provides stable amorphous form of sacubitril valsartan trisodium complex.

The term "stable amorphous form of sacubitril valsartan trisodium complex form refers to" amorphous form of sacubitril valsartan trisodium complex in which the PXRD pattern of the amorphous form, the chromatographic purity, and the description do not change when stored at a temperature of 40° C.±2° C. and at a relative humidity of 75%±5% for three months or more.

In another embodiment, the stable amorphous form of sacubitril valsartan trisodium complex of the present invention remains stable and does not convert to any other solid form when stored at a temperature of up to about 40° C. and at a relative humidity of about 25% to about 75% for about three months or more.

The amorphous form of sacubitril valsartan trisodium complex is stable when subjected to the real time and accelerated conditions, wherein the amorphous form of sacubitril valsartan trisodium complex is stored at 25±2° C./60±5% RH for a period 6 months and at 40±2° C./75±5% RH for a period of 6 months.

In another embodiment, the present invention provides processes for the preparation of amorphous form of sacubitril valsartan trisodium complex.

In another embodiment, the present invention provides a process for preparation of stable amorphous form of sacubitril valsartan trisodium complex, comprising:
a) providing a solution or suspension of valsartan sodium and sacubitril sodium salt in a suitable solvent (S1),
b) removing the solvent from the step a) reaction mass,
c) optionally adding a suitable solvent (S2) to the step b); and
d) isolating the amorphous form.

The starting compounds valsartan sodium, preferably its disodium salt and sacubitril sodium salts were known in the art and can be prepared by any known methods. Alternatively the starting compounds valsartan disodium and sacubitril sodium salt can be prepared according to the process disclosed in the present invention herein below.

The step a) of providing a solution or suspension of valsartan disodium and sacubitril sodium salt may include dissolving valsartan disodium and sacubitril sodium salt in a suitable solvent (S1) at a suitable temperature of at about 25° C. to about reflux. The suitable solvent (S1) include, but are not limited to ketones, alcohols, amides, sulfoxides, ethers and mixtures thereof. The ketones include, but are not limited to acetone, methylisobutylketone, methylethylketone and the like; alcohols include, but are not limited to methanol, ethanol, propanol, isopropanol, butanol and the like; amides include, but are not limited to dimethyl formamide, dimethyl acetamide, N-methyl pyrrolidinone and the like; sulfoxides include, but are not limited to dimethyl sulfoxide, diethyl sulfoxide and the like; ethers include, but are not limited to tetrahydrofuran, dimethyl ether, diethyl ether, diisopropyl ether, methyl tertiary butyl ether, 1,4-dioxane and the like and mixtures thereof; preferably the suitable solvent (S1) is acetone or ethanol.

In order to form a solution of step a), the contents may be stirred for sufficient period of time at a suitable temperature of at about 25° C. to about reflux. Typically, the contents were stirred for about 10 min to about 2 hrs at a temperature of 25-35° C.

Step b) of the aforementioned process involves removal of solvent from the solution by, for example, substantially complete evaporation of the solvent, concentrating the solution to obtain amorphous form as a solid or semi-solid. Evaporation can be achieved by a distillation, lyophilisation or freeze-drying technique, rotational drying (such as with the Buchi Rotavapor), spray drying, fluid bed drying, flash drying, spin flash drying, agitated thin-film drying and the like. Preferably, the solvent may be removed completely by distillation under vacuum at a temperature of about 25° C. to about 60° C.

If the resultant compound is a semi-solid compound, then it may be further treated with a suitable solvent (S2) at a temperature of about 15° C. to about 50° C. to obtain substantially a solid compound. Preferably, the addition of suitable solvent (S2) is carried out at a temperature of 15-35° C. The suitable solvent (S2) include, but are not limited to water, ethers, aliphatic hydrocarbons, alicyclic hydrocarbons and the like and mixtures thereof. The ethers include, but are not limited to tetrahydrofuran, dimethyl ether, diethyl ether, diisopropyl ether, methyl tertiary butyl ether, 1,4-dioxane and the like; aliphatic hydrocarbons include, but are not limited to hexane, heptane, propane and the like; alicyclic hydrocarbons include, but are not limited to cyclopropane, cyclobutane, cyclopentane, cyclohexane, methyl cyclohexane, cycloheptane, cyclooctane and the like, water and mixture thereof; preferably the suitable solvent (S2) is cyclohexane or heptane.

The isolation of amorphous form of sacubitril valsartan trisodium complex may be carried out by any conventional techniques known in the art for example filtration. Typically, if stirring is involved, the temperature during stirring can range from about 0° C. to about 30° C., preferably at about 10° C. to about 25° C.

The amorphous form of sacubitril valsartan trisodium complex obtained by the above process may be dried for about 2 hours to 25 hours. Drying can be suitably carried out in a vacuum tray dryer, vacuum oven, air oven, Rotocon Vacuum Dryer, Vacuum Paddle Dryer fluidized bed drier, spin flash dryer, flash dryer and the like.

In another embodiment, the present invention provides a process for preparation of amorphous form of sacubitril valsartan trisodium complex, comprising:
a) providing a solution or suspension of trisodium sacubitril valsartan complex in a suitable solvent (S1),
b) removing the solvent from the step a) reaction mass,
c) optionally adding a suitable solvent (S2) to the step b); and
d) isolating the amorphous form.

The starting compound trisodium sacubitril valsartan complex is known in the art and can be prepared by any known method, for example U.S. Pat. No. 887,793.

The step of providing a solution of trisodium sacubitril valsartan complex in a suitable solvent (S1), removal of solvent, addition of a suitable solvent (S2) and the isolation procedures can be followed as procedures described just as above.

The sacubitril valsartan trisodium complex recovered from the above processes is substantially in an amorphous form and is remains stable when stored at a temperature of up to 40±2° C. and at relative humidity of up to 75±5% for 6 months.

In another embodiment, the present invention provides an amorphous solid dispersion of sacubitril valsartan trisodium complex.

In accordance with another embodiment, the present invention provides amorphous solid dispersion of sacubitril valsartan trisodium complex with one or more pharmaceutically acceptable carrier.

It is observed that known amorphous form was highly hygroscopic in nature and is becomes deliquescent at room temperatures itself. The inventors of the present invention have found that stability of amorphous sacubitril valsartan trisodium complex may be increased by including amorphous sacubitril valsartan trisodium complex in to the inner cavity of at least one pharmaceutically acceptable carrier, where they are protected from external influences.

The pharmaceutically acceptable carriers includes but are not limited to hydrophilic carriers such as polymers of N-vinylpyrrolidone commonly known as polyvinylpyrrolidine or "PVP," or povidone, copovidone, meglumine, gum, cellulose derivatives such as microcrystalline cellulose (MCC), methyl cellulose, ethyl cellulose, hydroxypropyl cellulose (HPC or hypromellose), hydroxypropyl methylcellulose (HPMC), hydroxypropyl ethyl cellulose (HPEC), cyclodextrins, gelatin, hypromellose phthalate, lactose, polyhydric alcohols, polyethylene glycols (PEG), polyethylene oxides, polyoxyalkylene derivatives, methacrylic acid copolymers, polyvinyl alcohols, and propylene glycol derivatives, fatty acids, fatty alcohols, or esters of fatty acids; or its derivatives thereof.

Useful pyrrolidones include, but are not limited to homopolymers or copolymers of N-vinylpyrrolidone. Such polymers can form complexes with a variety of compounds. The water-soluble forms of N-vinylpyrrolidone are available in a variety of viscosity and molecular weight grades such as but not limited to PVP K-12, PVP K-15, PVP K-17, PVP K-25, PVP K-30, PVP K-90, PVP K-120 and crospovidone.

Polyethylene glycols, condensation polymers of ethylene oxide and water, are commercially available from various manufacturers in average molecular weights ranging from about 300 to about 10,000,000 Daltons. Some of the grades that are useful in the present invention include, but are not limited to, PEG 1500, PEG 4000, PEG 6000, PEG 8000, etc.

Among various cyclodextrins α-, β-, γ- and ε-cyclodextrins or their methylated or hydroxyalkylated derivatives may be used. Methods for preparation of the granulates are described below. Similar preparative process can be used irrespective of whether α-, β-, γ- and ε-cyclodextrins, or their methylated or hydroxyalkylated derivates are used.

Any pharmaceutical carrier will be acceptable as long as it allows the formation of the stable amorphous solid dispersion of sacubitril valsartan trisodium complex as described herein, is compatible with the sacubitril valsartan trisodium complex, and is acceptable for human pharmaceutical use. The choice of carrier is within the scope of understanding of a person skilled in the art and is not limited by the list of carriers above.

Preferably the pharmaceutically acceptable carriers are povidone, copovidone, cyclodextrins, lactose, hydroxypropyl cellulose, hydroxypropyl methyl cellulose, ethyl cellulose, or polyethylene glycol; more preferably the pharmaceutically acceptable carriers are povidone, copovidone, (2-hydroxy propyl)-β-cyclodextrin, lactose, hydroxypropyl cellulose or hydroxypropyl methyl cellulose.

In another embodiment, the amorphous solid dispersion of sacubitril valsartan trisodium complex with pharmaceutically acceptable carrier of the present invention is stable when subjected to the real time and accelerated conditions, wherein the amorphous solid dispersion of sacubitril valsartan trisodium complex with a pharmaceutically acceptable carrier is at 25±2° C./60±5% RH and at 40±2° C./75±5% RH for a period of 3 months or more.

In another embodiment, the present invention provides a process for preparation of amorphous solid dispersion of sacubitril valsartan trisodium complex with one or more pharmaceutically acceptable carrier; wherein the pharmaceutically acceptable carriers are described as above.

The reported processes involve the preparation of solid dispersion by dissolving sacubitril valsartan trisodium complex and a pharmaceutically acceptable carrier in a suitable solvent followed by isolation. This process introduced additional steps of sacubitril valsartan trisodium complex preparation from sacubitril free acid and valsartan free acid and isolation of resulting sacubitril valsartan trisodium complex. The isolated complex is again treated with a pharmaceutically acceptable carrier in a suitable solvent that makes the process lengthy and not viable on commercial scale. In order to avoid these difficulties the present inventors have developed a simple process, wherein the process involves treating sacubitril sodium and valsartan disodium salts directly with one or more pharmaceutically acceptable carrier in a suitable solvent followed by isolation.

In another embodiment, the present invention provides a process for the preparation of amorphous solid dispersion of sacubitril valsartan trisodium complex with one or more pharmaceutically acceptable carrier, which comprising:
a) providing a solution or suspension of valsartan sodium, sacubitril sodium salt and one or more pharmaceutically acceptable carrier in a suitable solvent (S3) or mixture of solvents, and
b) isolating the amorphous solid dispersion; wherein the pharmaceutically acceptable carrier comprises one or more of a povidone, copovidone, meglumine, gum, ethyl cellulose, hydroxypropyl cellulose, hydroxypropyl methyl cellulose, hydroxypropyl ethyl cellulose, microcrystalline cellulose, cyclodextrin, gelatin, hypromellose phthalate, lactose, polyhydric alcohol, polyethylene glycol, polyethylene oxide, polyoxyalkylene derivative, methacrylic acid copolymer, polyvinyl alcohol, propylene glycol derivative, fatty acid, fatty alcohols, or esters of fatty acids; and wherein the suitable solvent (S3) is selected from the group consisting of water, alcohols and ketones and the like and mixtures thereof.

The starting compounds valsartan sodium, preferably its disodium salt and sacubitril sodium salts were known in the art and can be prepared by any known methods. Alternatively the starting compounds valsartan disodium and sacubitril sodium salt can be prepared according to process disclosed herein present invention.

The step a) of providing a solution or suspension may include dissolution of valsartan disodium, sacubitril sodium salt and one or more pharmaceutically acceptable carrier as described above, in a suitable solvent (S3) or mixture of solvents at a suitable temperature of at about 25° C. to about reflux. The suitable solvent (S3) used for dissolution is selected from the group consisting of water, alcohols such as methanol, ethanol, isopropanol and the like; ketone solvents such as acetone, methylisobutylketone, methylethylketone and the like; and mixtures thereof; preferably the suitable solvent (S3) is water, methanol, ethanol, acetone and mixtures thereof.

Preferably, the pharmaceutically acceptable carrier used herein selected from the group consisting of povidone, copovidone, cyclodextrins, lactose, hydroxypropyl cellulose, hydroxypropyl methyl cellulose, ethyl cellulose, or polyethylene glycol; more preferably povidone, copovidone, (2-hydroxy propyl)-β-cyclodextrin, lactose, hydroxypropyl cellulose or hydroxypropyl methyl cellulose; still more preferably povidone, copovidone, hydroxypropyl cellulose or hydroxypropyl methyl cellulose.

In order to form a solution of step a), the contents may be stirred for sufficient period of time at about 25° C. to about reflux. Typically, the contents were stirred for about 10 min to about 30 min for complete dissolution.

In step b) of isolation of solid dispersion of amorphous sacubitril valsartan trisodium complex can be carried out by removal of solvent or cooling the solution to precipitation or by addition of anti-solvent to precipitation followed by filtration.

The isolation of the resultant product is accomplished by removal of the solvent from the solution by, for example, substantially complete evaporation of the solvent, concentrating the solution, cooling to obtain amorphous form and filtering the solid under inert atmosphere. Alternatively, the solvent may also be removed by evaporation. Evaporation can be achieved at sub-zero temperatures by the lyophilisation or freeze-drying technique, a rotational drying (such as with the Buchi Rotavapor), spray drying, fluid bed drying, flash drying, spin flash drying and thin-film drying. Preferably, the solvent may be removed completely by distillation under vacuum at a temperature of about 25° C. to about 60° C.

The resultant amorphous solid dispersion of sacubitril valsartan trisodium complex may optionally be dried. Drying can be suitably carried out in a tray dryer, vacuum oven, air oven, fluidized bed drier, spin flash dryer, flash dryer and the like.

Alternatively, amorphous solid dispersion of sacubitril valsartan trisodium complex may also be prepared by providing a solution of sacubitril valsartan trisodium complex and one or more pharmaceutically acceptable carrier in a suitable solvent (S3) or mixture of solvents and isolating the amorphous solid dispersion. The step of providing a solution of sacubitril valsartan trisodium complex and one or more pharmaceutically acceptable carrier in a suitable solvent (S3) or mixture of solvents and the isolation procedures are according to procedure described just as above.

The amorphous solid dispersion of sacubitril valsartan trisodium complex of the present invention has commercially acceptable pharmacokinetic characteristics, solubility, flow properties, stability, and the like. The products may optionally be milled to get the desired particle size distributions. Milling or micronization may be performed prior to drying, or after the completion of drying of the products. The milling operation reduces the size of particles and increases surface area of particles by colliding particles with each other at high velocities.

The present invention provides amorphous solid dispersion of sacubitril valsartan trisodium complex recovered from the process described as above is an amorphous solid dispersion of sacubitril valsartan trisodium complex with hydroxypropyl methylcellulose (HPMC), an amorphous solid dispersion of sacubitril valsartan trisodium complex with hydroxypropyl cellulose (HPC), an amorphous solid dispersion of sacubitril valsartan trisodium complex with povidone or an amorphous solid dispersion of sacubitril valsartan trisodium complex with copovidone.

In another embodiment, the present invention provides an amorphous solid dispersion of sacubitril valsartan trisodium complex with hydroxypropyl methylcellulose (HPMC).

Figure 6:
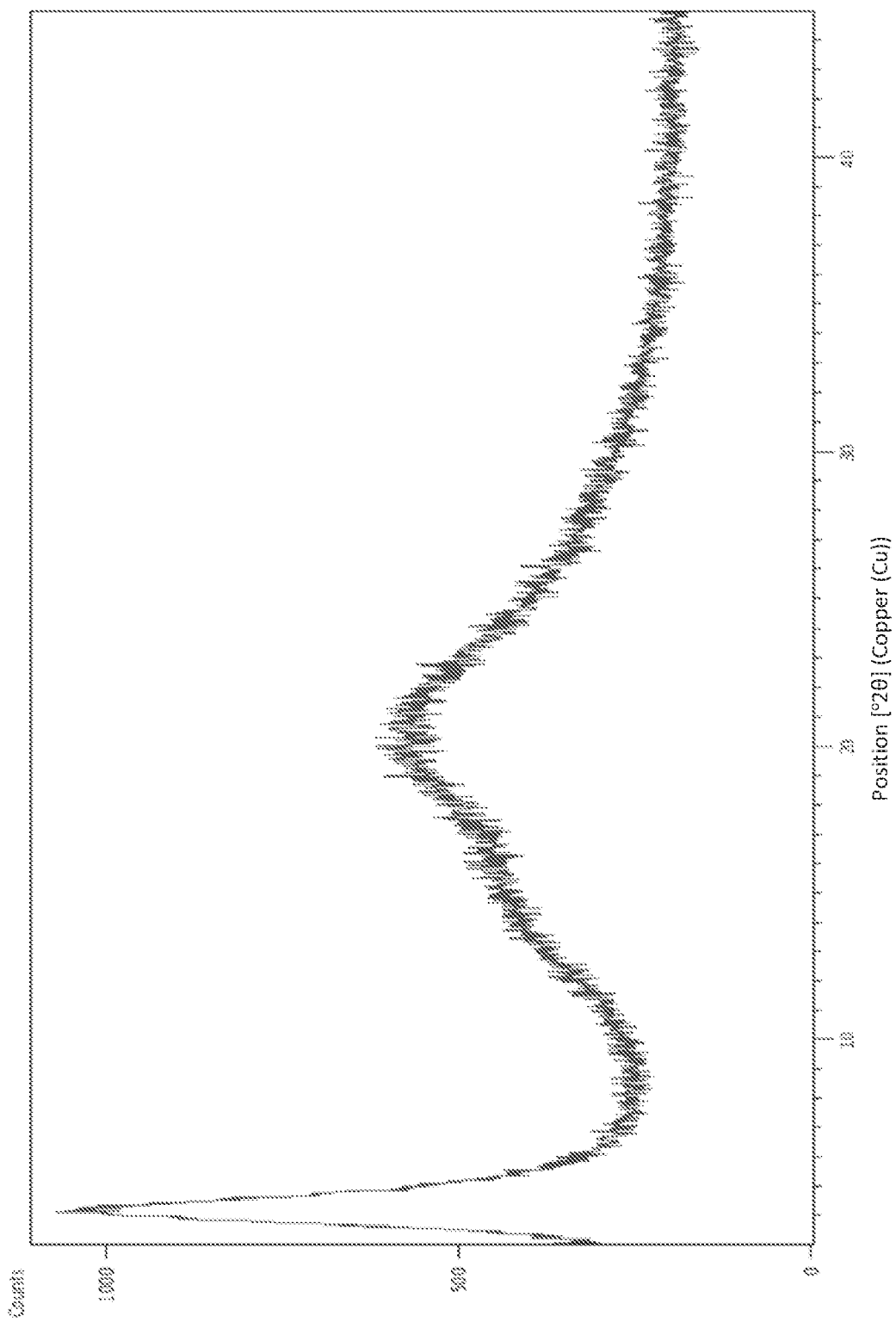
FIG. 6 is the characteristic powder X-ray diffraction (XRD) pattern of amorphous solid dispersion of sacubitril valsartan trisodium complex with hydroxypropyl methylcellulose prepared according to Example-11.
Figure 7:
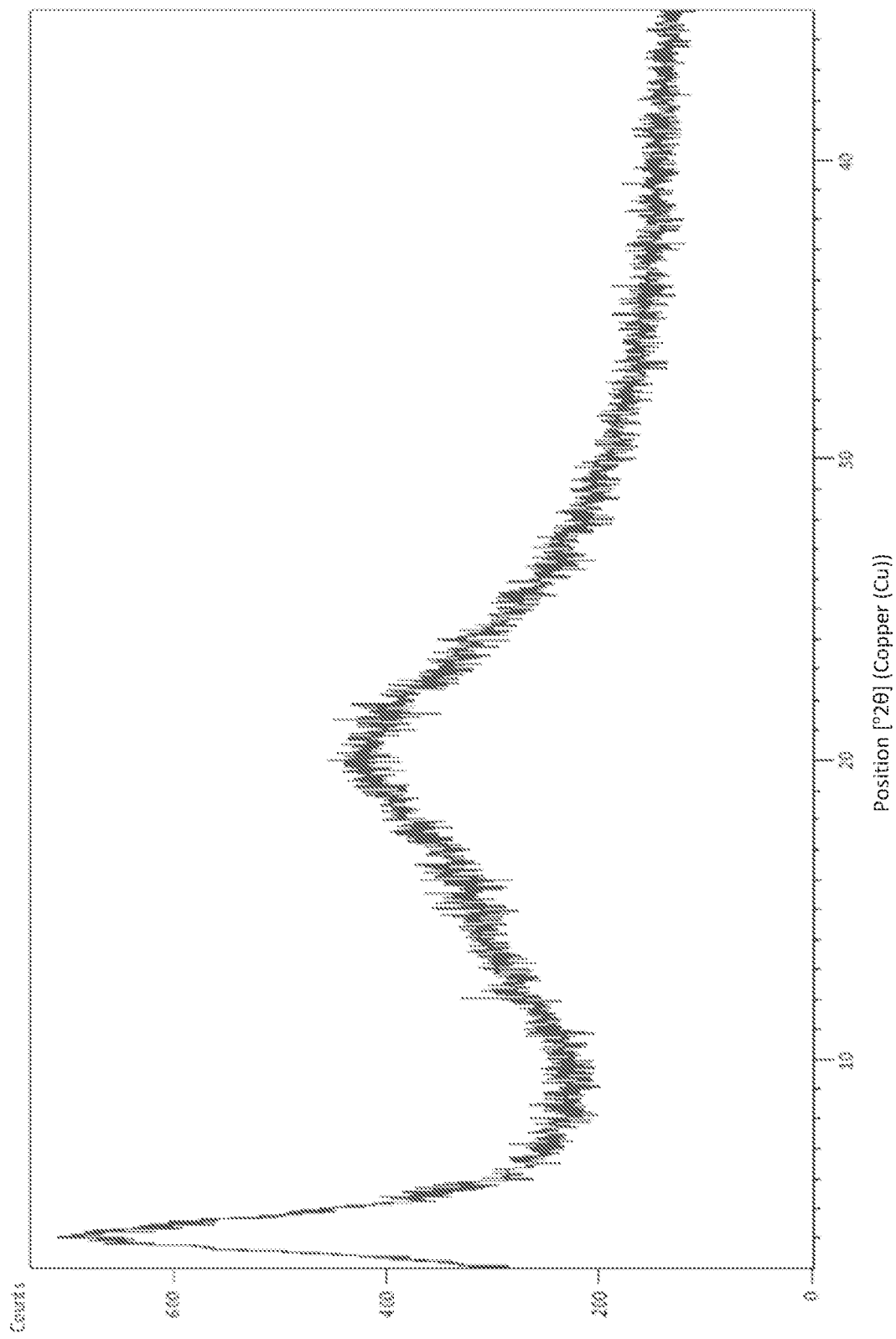
FIG. 7 is the characteristic powder X-ray diffraction (XRD) pattern of amorphous solid dispersion of sacubitril valsartan trisodium complex with hydroxypropyl methylcellulose prepared according to Example-12.

In another embodiment, the present invention provides amorphous solid dispersion of sacubitril valsartan trisodium complex with hydroxypropyl methylcellulose (HPMC) characterized by a powder X-Ray diffraction (PXRD) pattern substantially in accordance with FIGS. 6 & 7.

In another embodiment, the present invention provides amorphous solid dispersion of sacubitril valsartan trisodium complex with hydroxypropyl cellulose (HPC).

Figure 8:
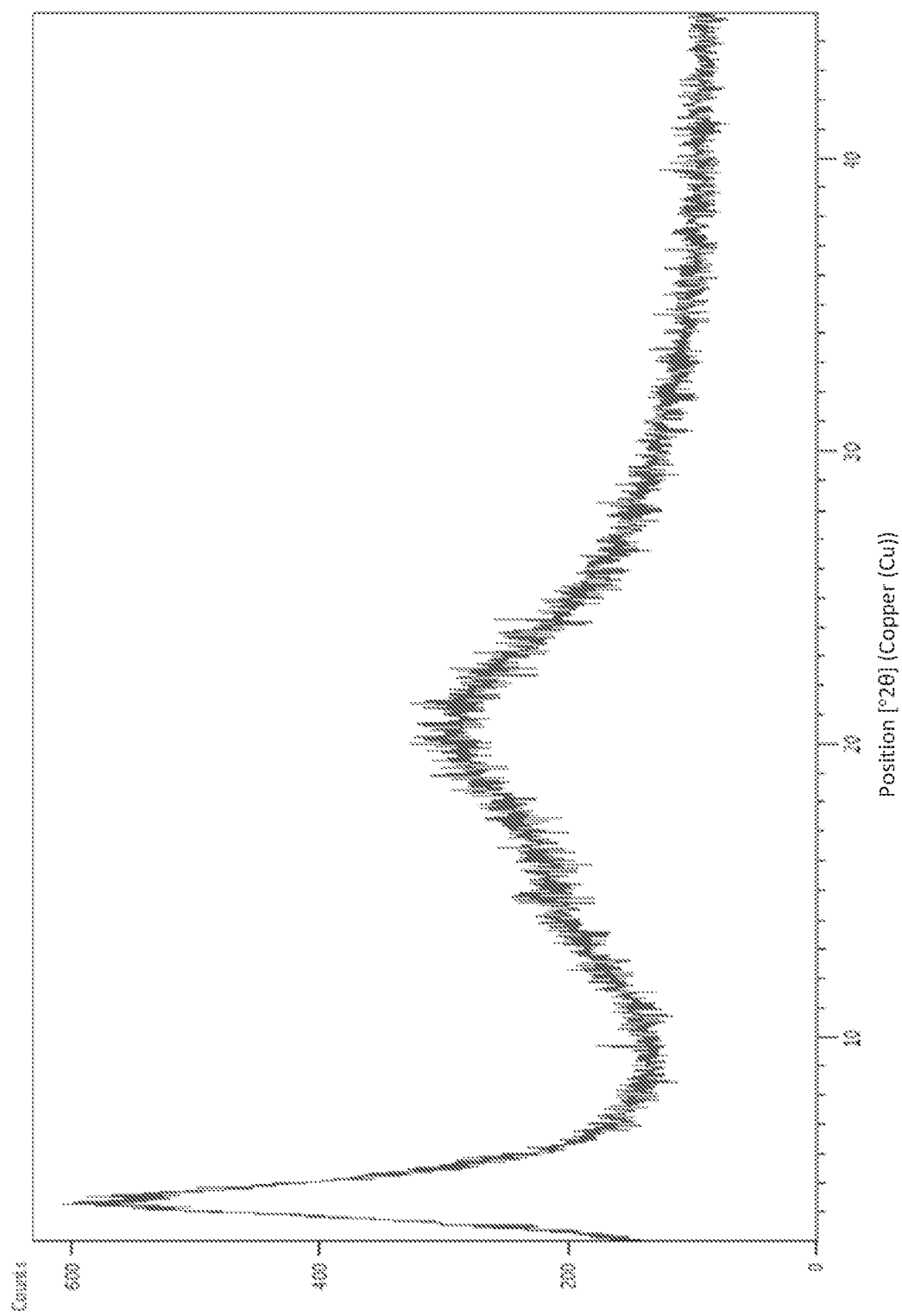
FIG. 8 is the characteristic powder X-ray diffraction (XRD) pattern of amorphous solid dispersion of sacubitril valsartan trisodium complex with hydroxypropyl cellulose prepared according to Example-19.

In another embodiment, the present invention provides amorphous solid dispersion of sacubitril valsartan trisodium complex with hydroxypropyl cellulose (HPC) characterized by a powder X-Ray diffraction (PXRD) pattern substantially in accordance with FIG. 8.

In another embodiment, the present invention provides amorphous solid dispersion of sacubitril valsartan trisodium complex with copovidone.

Figure 10:
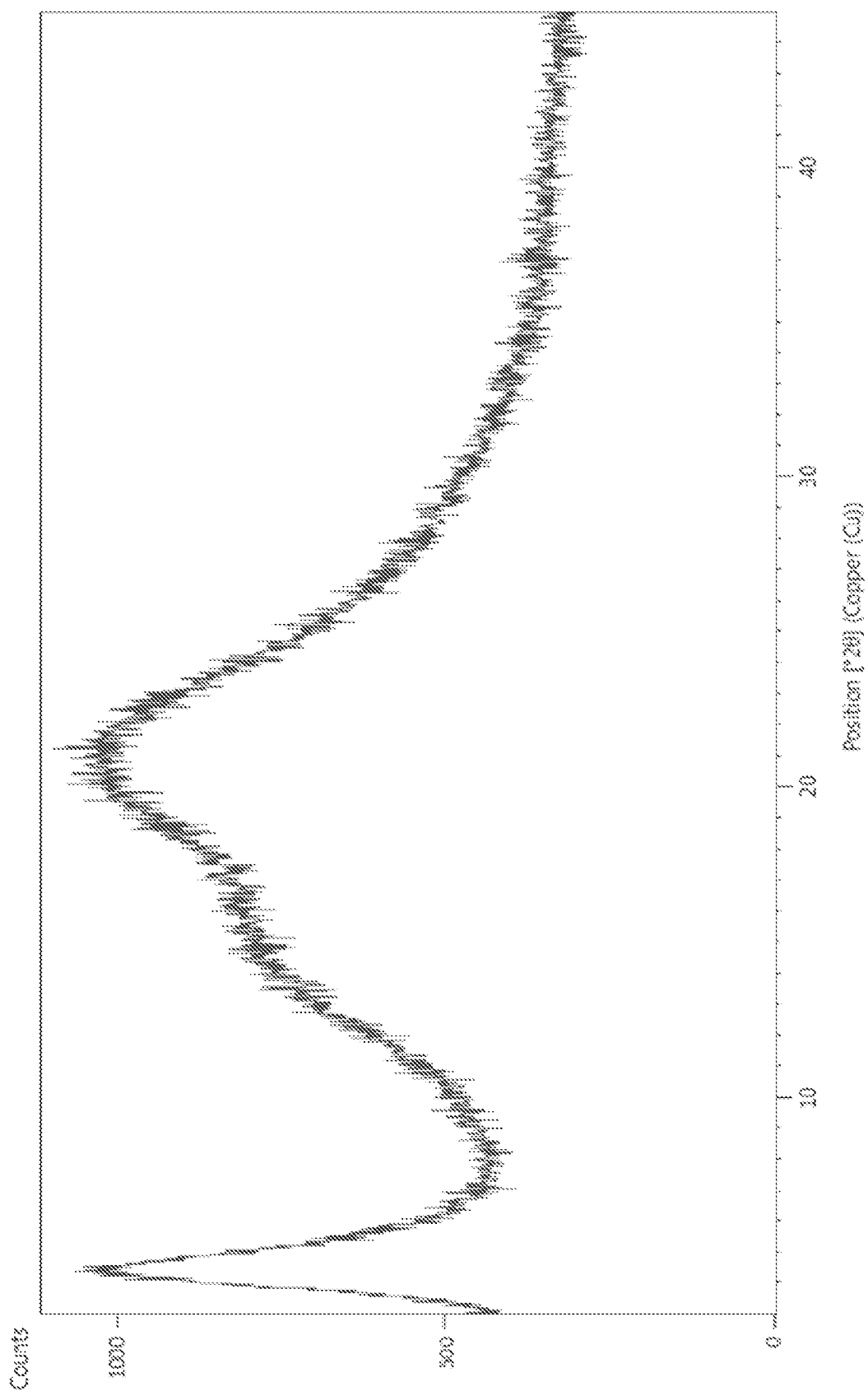
FIG. 10 is the characteristic powder X-ray diffraction (XRD) pattern of amorphous solid dispersion of sacubitril valsartan trisodium complex with copovidone according to Example-23.

In another embodiment, the present invention provides amorphous solid dispersion of sacubitril valsartan trisodium complex with copovidone characterized by a powder X-Ray diffraction (PXRD) pattern substantially in accordance with FIG. 10.

In another embodiment, the present invention provides amorphous solid dispersion of sacubitril valsartan trisodium complex with povidone.

Figure 11:
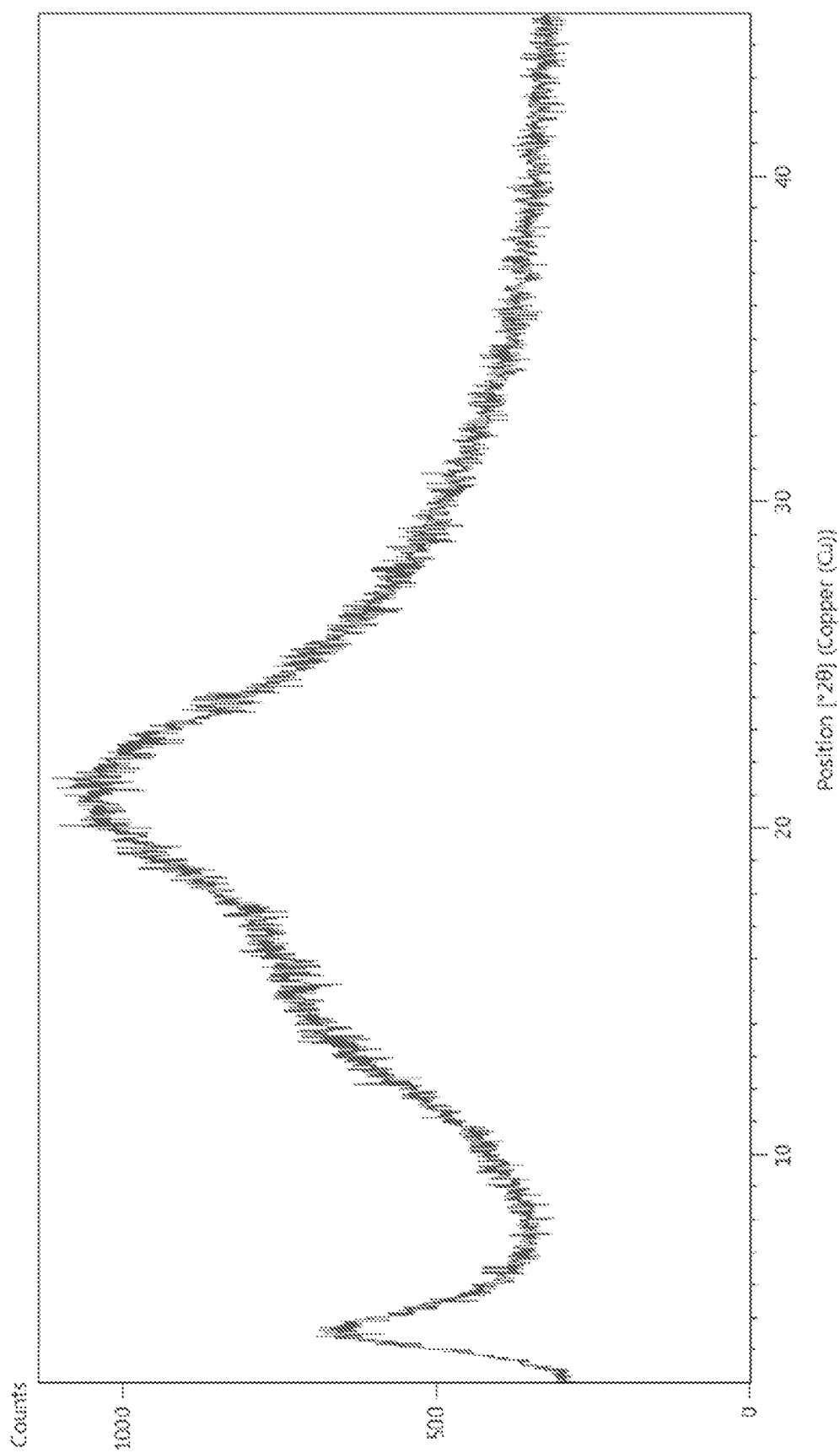
FIG. 11 is the characteristic powder X-ray diffraction (XRD) pattern of amorphous solid dispersion of sacubitril valsartan trisodium complex with povidone according to Example-25.

In another embodiment, the present invention provides amorphous solid dispersion of sacubitril valsartan trisodium complex with povidone characterized by a powder X-Ray diffraction (PXRD) pattern substantially in accordance with FIG. 11.

The amorphous solid dispersion of sacubitril valsartan trisodium complex with at least one pharmaceutically acceptable carrier is stable during storage. This property is important and advantageous for the desired use of sacubitril valsartan trisodium complex in pharmaceutical product formulations.

The amorphous solid dispersion of sacubitril valsartan trisodium complex with pharmaceutically acceptable carrier of the present invention is stable when subjected to the stability at 25±2° C./60±5% RH and at 40±2° C./75±5% RH for a period of 3 months or more.

In another embodiment, the present invention provides a process for preparation of sacubitril sodium salt of formula II, Formula II

[Chemical structure of sacubitril sodium salt]

comprising:
a) reacting a compound of formula III with a suitable halogen source in presence of ethanol and a suitable non-polar solvent to obtain a compound of formula IV or its acid addition salt thereof;

Formula III

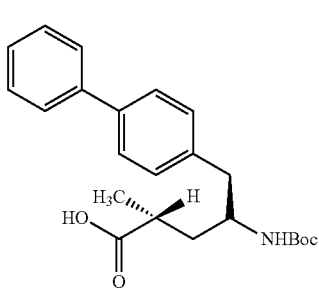

Formula IV

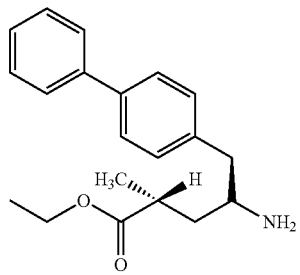

b) treating the compound of formula IV or its acid addition salt with succinic anhydride in the presence of a base to obtain sacubitril of formula V; and Formula V

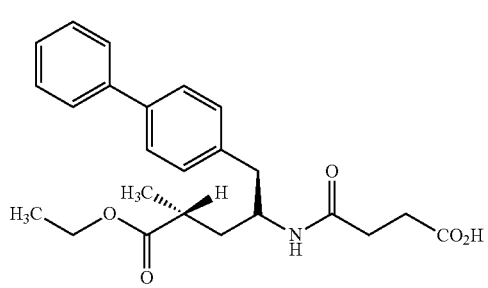

c) treating the sacubitril of formula V with a suitable sodium source to obtain sacubitril sodium of formula II.

The starting material of Formula III is known in the art and can be prepared by any known method, for example WO2008/031567.

Step a) of the aforementioned process involves the reaction of a compound of formula III with a suitable halogen source in the presence of ethanol and a non-polar solvent to obtain a compound of formula IV or its acid addition salt thereof. The suitable halogen source used herein for step a) is selected from the group consisting of thionyl chloride, oxalyl chloride, phosgene, acetyl chloride and the like; preferably thionyl chloride.

The suitable temperature for step a) reaction is about 25° C. to about reflux temperature of the solvent used. Any other temperatures may also be acceptable, provided a clear solution of the concerned materials is obtained in the solvents chosen; preferably the step a) reaction is carried out at temperature of about 40° C. to about 50° C.

The step a) reaction is usually carried out in the reported literatures are in presence of ethanol and thionyl chloride. Due to the presence of moisture during the reaction leads to the formation of amine-acid impurity of formula A.

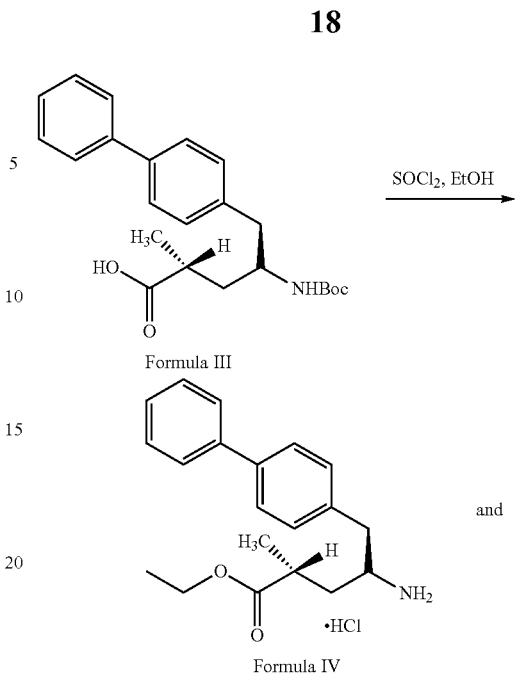

Formula III

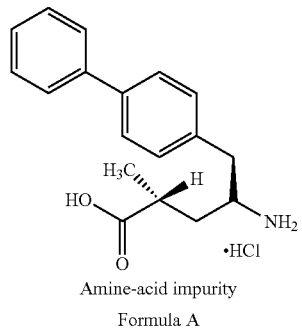

and

Formula IV

Amine-acid impurity
Formula A

The impurity of Formula A once formed in the reaction, it is difficult to remove and is transformed into desethyl sacubitril impurity of Formula B in the subsequent stages of the reaction, if untreated at this stage. Therefore repeated purifications are required to get pure intermediate of Formula IV as well as sacubitril of Formula V.

Formula B

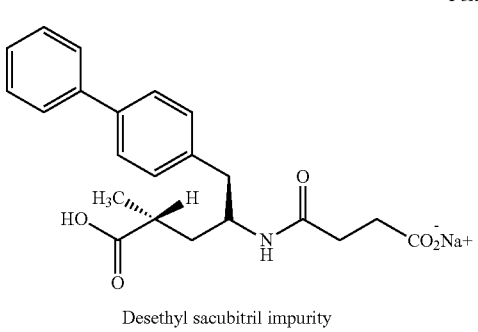

Desethyl sacubitril impurity

The present inventors have studied the effect of solvent in step a) reaction with respect to impurity generation. It is observed that when step a) reaction is carried out only in ethanol, the content of acid-amine impurity of Formula A is in the range of 0.5-1%. Whereas when the same reaction is carried out with ethanol in presence of non-polar solvents, the impurity formation is minimized to below 0.1%. Therefore, the present invention provides an improved process for the preparation of sacubitril sodium salt of Formula II with low content of impurity of Formula A by reacting a compound of formula III with a suitable halogen source in presence of ethanol and a suitable non-polar solvent.

In a preferred embodiment, the step a) reaction is carried out in the presence of ethanol and a non-polar solvent.

The non-polar solvent used herein for step a) is selected from the group consisting of cyclohexane, heptane, hexane, dichloromethane, toluene and the like; and mixtures thereof; preferably the non-polar solvent is cyclohexane.

In an embodiment, the step a) reaction when carried out in a mixture of ethanol and cyclohexane the resulted compound is having less than 0.1% of impurity of Formula A.

After completion of reaction, the resultant compound of formula IV is isolated. The isolation step involves distillation of the solvent completely from the reaction mixture under reduced pressure at below 40° C. and the obtained residue may be co-distilled with the non-polar solvent. The resulting solid may be further treated with a mixture of ethanol and non-polar solvent at a temperature of about 25-35° C. and isolating the compound of Formula IV by techniques known in the art, for example, filtration.

Step b) of the aforementioned process involves, treating the compound of formula IV or its acid addition salt with succinic anhydride in the presence of base and solvent to obtain the sacubitril of formula V.

The base used herein for step b) is selected from the group consisting of diethylamine, triethylamine, diisopropylamine, diisopropylethylamine, pyridine, piperidine, morpholine and DBU; preferably the base is triethylamine.

The suitable solvent includes dichloromethane, dimethylformamide, dimethylacetamide, dimethylsulfoxide, N-methylpyrrolidone, acetonitrile, tetrahydrofuran, 2-methyltetrahydrofuran and the like; preferably the suitable solvent is dichloromethane.

The inventors of the present invention have surprisingly found that addition of base in a controlled manner such as lot wise addition (multiple lots) at a temperature of below 10° C. are considerably favorable to minimize the formation of the lactam impurity of Formula C.

Formula C

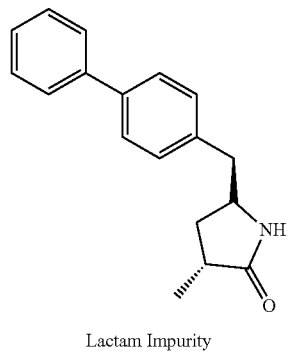

Lactam Impurity

It has been observed that impurity of Formula C is produced when the addition of base is carried out at above 10° C. Hence, to achieve a high efficiency of the reaction, it is necessary to minimize the formation of the impurity of formula C which is achieved by the present invention by controlling the addition temperature at less than 10° C.

In another embodiment, the present invention provides the addition of base in a controlled manner such as lot wise addition at a temperature of below 10° C. in order to avoid the formation of lactam impurity of Formula C.

After completion of the reaction, the resultant sacubitril of Formula V thus formed can be isolated or further processed without isolating into next reaction.

Preferably after completion of the reaction, the reaction mass may be treated with dilute hydrochloric acid and the layers were separated. The aqueous layer may be extracted with dichloromethane and the product containing organic layer proceed further without isolating in to subsequent reactions.

Conversion of sacubitril of Formula V into its sodium salt of Formula II is carried out with a suitable sodium source in presence of water.

The suitable sodium source is selected from the group consisting of sodium carbonate, sodium bicarbonate, and sodium 2-ethyl hexanoate; preferably the suitable sodium source is sodium carbonate or sodium bicarbonate.

The conversion of sacubitril of Formula V into its sodium salt is carried out at a temperature of about 25° C. to about 35° C.

The inventors of the present invention have found that when strong base such as sodium hydroxide is used for saltification of sacubitril gave higher amount of desethyl sacubitril impurity of Formula B by cleavage of ester group, which once formed is carried forward in to subsequent reaction steps and resulting Sacubitril of low purity and it is difficult to remove from the final API which requires additional crystallization steps to remove this impurity.

Thus in order to avoid the formation of desethyl sacubitril impurity of Formula B, the present inventors involved the use of mild bases such as sodium carbonate or sodium bicarbonate, which process selectively forming sodium salt with sacubitril compound of Formula V without hydrolysing the ester group.

After completion of the reaction, the resultant sacubitril sodium salt of Formula II is isolated. The isolation step involves distillation off the solvent completely from the reaction mass and the resulting residue is stripped off with ketone solvent; preferably with methyl ethyl ketone to obtain sacubitril sodium salt of Formula II.

The sacubitril sodium salt of Formula II thus obtained by the process of the present invention may contain des ethyl sacubitril of formula B is less than 0.1%, lactam impurity of Formula C is less than about 1% and succinamide impurity of Formula D is less than 0.2% by HPLC:

Formula D

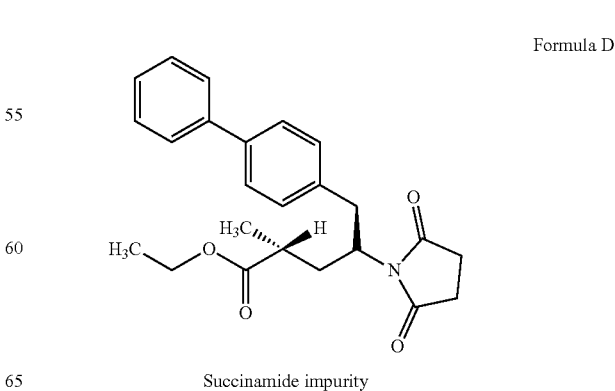

Succinamide impurity

Without removing these impurities at this stage of the synthesis, the same may carry forward to further steps in subsequent reactions and generates corresponding impurities in each stage up to the formation of final sacubitril valsartan trisodium complex, as a result getting the final product with low product yields and purity. In order to remove these impurities from each stage of the synthesis requires multiple purification processes that make the process lengthy and not viable on commercial scale.

The present inventors have found that purification of sacubitril sodium salt of Formula II using a novel solvent system efficiently remove the above impurities and obtained high pure sacubitril sodium salt of Formula II thereby getting high pure sacubitril valsartan trisodium complex using the pure sacubitril sodium salt compound of Formula II.

Thus the present invention provides the purification of sacubitril sodium salt of Formula II in order to avoid repetitive purifications to separate impurities in each stage of the synthesis up to the final sacubitril valsartan trisodium complex; particularly for the preparation of amorphous form of sacubitril valsartan trisodium complex.

In another embodiment, the present invention provides a process for purification of a sacubitril sodium salt of Formula II using a novel solvent system.

In accordance with another embodiment, the present invention provides a process for purification of sacubitril sodium salt of Formula II, comprising:
  i) dissolving sacubitril sodium salt of Formula II in one or more solvents,
  ii) optionally adding an antisolvent to the step i) reaction mixture or vice-versa, and
  iii) isolating the pure sacubitril sodium salt of Formula II;
wherein the one or more solvents are selected from the group consisting ketones, esters, halogenated hydrocarbons and the like and mixtures thereof, wherein the antisolvent is selected from the group consisting of ethers, aromatic hydrocarbons, aliphatic or cyclic hydrocarbons and mixtures thereof.

The step i) of the aforementioned process may include dissolving sacubitril sodium salt of Formula II in one or more solvents at a suitable temperature. Examples of one or more solvents of step i) includes but are not limited to ketones such as acetone, methyl isobutyl ketone, methyl ethyl ketone and the like; esters such as methyl acetate, ethyl acetate, isopropyl acetate, n-propyl acetate, n-butyl acetate, t-butyl acetate and the like; halogenated hydrocarbons such as dichloromethane, dichloroethane, chloroform and the like and mixtures thereof; preferably methyl ethyl ketone.

The suitable temperature for step i) reaction is about 20° C. to about reflux temperature of the solvent used. Any other temperatures may also be acceptable, provided a clear solution of the concerned materials is obtained in the solvents chosen; preferably the step i) reaction is carried out at temperature of about 45° C. to about 75° C.

Step ii) of the aforementioned process involves precipitation of sacubitril sodium of Formula II by either addition of suitable antisolvent to the step i) solution or addition of step i) solution into a suitable antisolvent. Preferably antisolvent is added to the resulting solution containing compound of Formula II to effect the crystallization of the product.

The antisolvent used herein is selected from the group consisting of aromatic hydrocarbons, aliphatic or cyclic hydrocarbons, ethers and mixtures thereof. The aromatic hydrocarbons include, but are not limited to toluene, xylene and the like; aliphatic or cyclic hydrocarbons include, but are not limited to n-hexane, n-heptane, cyclohexane, cycloheptane and the like; ethers include, but are not limited to tetrahydrofuran, dimethyl ether, diisopropyl ether, methyl tertiary butyl ether, 1,4-dioxane and the like; and mixtures thereof; preferably the anti-solvent is n-heptane.

Then, the resulting reaction mass may be cooled to a temperature of about 25° C. to about 35° C. or lower to precipitate out the product.

The isolation of pure sacubitril sodium salt of Formula II can be carried out by conventional techniques, for example filtration. The resultant pure sacubitril sodium salt of Formula II may optionally be further dried at a temperature ranging from about 50° C. to about 60° C.

The pure sacubitril sodium salt of Formula II thus obtained according to purification process of the invention having less than 0.1% of each of desethyl sacubitril impurity of Formula B, lactam impurity of Formula C and succinamide impurity of Formula D as measured by HPLC.

In another embodiment, the present invention provides sacubitril sodium having less than 0.1% of one or more of desethyl sacubitril impurity of Formula B, lactam impurity of Formula C and succinamide impurity of Formula D as measured by HPLC.

In another embodiment, the pure sacubitril sodium salt of Formula II obtained according to the processes of the invention can be used as an intermediate or as a starting material in the preparation of sacubitril valsartan trisodium complex; particularly in the preparation of amorphous form of sacubitril valsartan trisodium complex.

In another embodiment, the present invention provides a process for the preparation of amorphous form of sacubitril valsartan trisodium complex, comprising reacting sacubitril sodium obtained by the process of the invention described just as above and valsartan sodium in a suitable solvent (51) according to the process described under one of the embodiment of the invention.

In another embodiment, the present invention provides sacubitril valsartan trisodium complex obtained by the processes as described just above having purity of about 98% or more, of about 99% or more, of about 99.5% or more as measured by high performance liquid chromatography (HPLC).

In another embodiment, the present invention provides sacubitril valsartan trisodium complex obtained by the processes as described just above having less than 0.1% of one or more of desethyl sacubitril impurity of Formula B, lactam impurity of Formula C and succinamide impurity of Formula D as measured by HPLC.

In another embodiment, the present invention provides amorphous from of sacubitril valsartan trisodium complex obtained by the processes as described just above having less than 0.1% of one or more of desethyl sacubitril impurity of Formula B, lactam impurity of Formula C and succinamide impurity of Formula D as measured by HPLC.

In another embodiment, the present invention provides an amorphous form of sacubitril valsartan trisodium complex obtained by the processes as described just above having purity of about 98% or more, of about 99% or more, of about 99.5% or more as measured by high performance liquid chromatography (HPLC) and having less than 0.1% of one or more of desethyl sacubitril impurity of Formula B, lactam impurity of Formula C and succinamide impurity of Formula D as measured by HPLC.

In another embodiment, the present invention provides a pharmaceutical composition comprising an amorphous form of sacubitril valsartan trisodium complex prepared by the process described above or an amorphous solid dispersion of sacubitril valsartan trisodium complex with at least one pharmaceutically acceptable carrier, together with one or more pharmaceutically acceptable excipients. Such pharmaceutical composition may be administered to a mammalian patient in any dosage form, e.g., solid, liquid, powder, injectable solution, etc.

In another embodiment, the present invention provides a method of packing amorphous form of sacubitril valsartan trisodium complex, comprising: placing amorphous form of sacubitril valsartan trisodium complex in LDPE bag under nitrogen atmosphere; placing the product containing Low-density polyethylene (LDPE) bag in a second LDPE bag under nitrogen atmosphere; keeping the silica gel packet between two LDPE bags and sealing; placing the second sealed bag in a triple laminated bag and sealing.

The amorphous form of sacubitril valsartan trisodium complex obtained by the processes of the invention is packed according to the above embodiment and stored for stability. A period of up to 6 months at real and accelerated conditions, the amorphous character was retained and does not convert to any other solid form when stored at a temperature of up to about 40° C. and at a relative humidity of about 25% to about 75%.

The X-Ray powder diffraction can be measured using PANalytical X'per³pro X-ray powder Diffractometer equipped with a Cu-anode ([λ]=1.54 Angstrom), X-ray source operated at 45 kV, 40 mA. Two-theta calibration is performed using an NIST SRM 640c Si standard. The sample was analyzed using the following instrument parameters: measuring range=3-45° 2θ; step size=0.01°; and Time per step=23 sec.

All DSC data reported herein were analyzed in hermitically sealed aluminium pan (with pin hole), with a blank hermitically sealed aluminium pan as the reference and were obtained using DSC (DSC Q200, TA instrumentation, Waters) at a scan rate of 10° C. per minute, Temperature range 50 to 280° C. with an Indium standard.

All TGA data reported herein were analyzed using TGA Q500 V 20.13 build 39 in platinum pan with a temperature rise of about 10° C./min in the range of Room temperature to 250° C.

IR spectrum were recorded using Perkin Elmer Spectrum-100, FT-IR spectrophotometer; Spectrum ES software. Potassium bromide, spectroscopy grade, Merck, Darmstadt, Germany, was used. Disk pelletization method was employed for sample preparation. The pellets were prepared by mixing the sample with potassium bromide (1:100) in a mortar and compressed at a pressure of 6 to 8 bar. Each spectrum was derived from four single averaged scans collected in the mid IR region of 4000-450 cm$^{-1}$ at a spectral resolution of 4.0 cm$^{-1}$.

In another embodiment, the present invention provides Sacubitril sodium and amorphous form of sacubitril-valsartan trisodium complex obtained by the above process, as analyzed using high performance liquid chromatography ("HPLC") with the conditions are tabulated below:

| | |
|---|---|
| Column | Chiralcel OJ, (150 mm) |
| Column temperature | 27° C. |
| Mobile phase | Mobile phase -A: triflouroacetic acid in Milli-Q water |
| | Mobile phase -B: Acetonitrile |
| Diluent | Acetonitrile and water (1:1) |
| Flow rate | 1.2 mL/min |
| Wave length | 254 nm |
| Injection volume | 20 μL |

Gradient Program:

| Time | Mobile Phase A | Mobile Phase B |
|---|---|---|
| 0 | 70 | 30 |
| 45 | 70 | 30 |
| 65 | 50 | 50 |
| 75 | 25 | 75 |
| 80 | 25 | 75 |
| 85 | 70 | 30 |
| 90 | 70 | 30 |

EXAMPLES

The following non limiting examples illustrate specific embodiments of the present invention. They are not intended to be limiting the scope of the present invention in any way.

Reference Example 1

Preparation of amorphous form of trisodium salt of sacubitril valsartan complex according process described under example-1 of U.S. Pat. No. 8,877,938.

Sacubitril free acid (1.0 gm), acetone (95 ml) was added into a round bottom flask and stirred for 5 min at 25-35° C. Valsartan (0.97 gms) was added and stirred for 5 min at 25-35° C. Aq sodium hydroxide solution (0.26 gms sodium hydroxide dissolved in 16.6 ml water at 25-35° C.) was added to the reaction mass at 25-35° C. and stirred the solution for 1 hr at 25-35° C. The solvent was distilled out completely at 35° C. under vacuum, dried the resulting solids under vacuum at 35° C. for 2 hrs and further dried under vacuum at 45° C. for 5 hrs to obtain amorphous form. Yield: 1.78 gms.

Amorphous Form obtained according to the reference example was analyzed by PXRD, DSC, TGA and IR and are represented according to FIG. 1, FIG. 2, FIG. 3, and FIG. 4 respectively.

Reference Example 2

Preparation of crystalline trisodium salt of sacubitril valsartan complex according process described under example-1 of U.S. Pat. No. 8,877,938.

Sacubitril free acid (20 gms) and valsartan free acid (20 gms) were dissolved in acetone (2000 ml) under stirring at 25-35° C. Aq sodium hydroxide solution (5.5 gms dissolved in 320 ml water) was added via addition funnel to the above reaction mass and stirred for 60 min at the same temperature. The obtained clear solution was concentrated under vacuum at 50° C. to obtained glassy solid. Acetone was charged to the solid residue under stirring and sonicated for 30 min. The reaction mass was kept a side for 12 hrs at below 30° C. The obtained solid was filtered under vacuum at 20±5° C. under nitrogen atmosphere. The wet material was washed with acetone (40 ml) and dried under vacuum at 45° C. for 6 hrs to obtain crystalline sacubitril valsartan complex. Yield: 32 gms. HPLC purity: 99.95%

Reference Example 3

Preparation of Sacubitril:

Isopropyl acetate (264 ml) and sacubitril hemicalcium salt (26.4 gms) were added in to a round bottom flask at 25-35° C. and stirred for 15 min at 25-35° C. Hydrochloric acid solution (2N, 74 ml) was added to the resulting reaction mass at 25-35° C., stirred for 20 min and separated the layers. The organic layer was washed with water (3×53 ml) and dried over sodium sulphate (10 gms), distilled out the solvent under vacuum at 40° C. and degassed for 2 hrs under vacuum at 40° C. to obtain Sacubitril. Yield: 24 gms.

Reference Example 4

Preparation of Sacubitril Sodium:
Sacubitril free acid (24 gms) and acetonitrile (48 ml) were added in to a round bottom at 20-30° C. and stirred for 20 min at 20-30° C. Sodium hydroxide solution (2.3 gms dissolved in 7.2 ml water) was added to the resulting reaction solution at 20-30° C. and stirred for 1 hr, distilled out the solvent under vacuum at 40° C. and degassed for 2 hrs under vacuum at 40° C. to obtain a solid. Methanol (100 ml) was added to the resulting solid at 25-35° C. and stirred for 20 min. The solvent was distilled out completely under vacuum at 35-45° C., degassed for 1 hr under vacuum at 35-45° C. and dried the solid under vacuum at 35-45° C. for 16 hrs to obtain sacubitril sodium salt. Yield: 22 gms.

Reference Example 5

Preparation of Valsartan Disodium:
Valsartan (50 gms) and methanol (100 ml) were added in to a round bottom at 25-35° C. and stirred for 15 min at 25-35° C. To the resulting solution, sodium hydroxide in methanol (9.2 gms sodium hydroxide in 400 ml methanol) was added at 25-35° C., stirred the reaction mixture at 25-35° C. for 30 min, distilled out the solvent completely under vacuum at 40-45° C. and degassed the solid for 2 hrs under vacuum at 40-45° C. to obtain Valsartan disodium salt. Yield: 56.3 gms.

Comparative Example

Preparation of Compound of Formula IV:
(2R,4S)-5-Biphenyl-4-yl-4-tert-butoxycarbonylamino-2-methylpentanoic acid of Formula III (50 g) and ethanol (500 ml) were added into a round bottom flask at 25-35° C. and stirred for complete dissolution. Thionyl chloride (19 ml) was added to the above reaction mass at 25-35° C. The temperature of reaction mass was raised to 70-75° C. and stirred for 3 h at the same temperature, then cooled to 30-40° C. and distilled off the solvent completely under vacuum at below 50° C. The resulting residue was stripped off with cyclohexane (125 mL×2) to obtain crude product. HPLC analysis revealed the content of amine-acid impurity of Formula A: about 0.5% to 1%.
Cyclohexane (500 mL) was added to the obtained above crude material at 25-35° C., stirred for 30 min. The obtained solid material was filtered, washed with cyclohexane (50 mL×2) and dried to provide the tile compound as hydrochloride salt. Yield: 44 gms. HPLC purity: 98.68%; Amine-acid impurity of Formula A: 0.38%.

Example 1

Preparation of Compound of Formula IV:
(2R,4S)-5-Biphenyl-4-yl-4-tert-butoxycarbonylamino-2-methylpentanoic acid of Formula III (100 gms) and ethanol (200 ml) were added into a round bottom flask at 25-35° C. and stirred for 60 mins. To this solution cyclohexane (500 ml) was added and then thionyl chloride (38 ml) was added slowly at 25-35° C. The temperature of the reaction mass was raised to 42-48° C., maintained for 7 hrs and distilled the solvent completely under reduced pressure at below 50° C. and then co-distilled the resulting residue with cyclohexane (300 ml*2). HPLC analysis revealed the content of amine-acid impurity of Formula A: 0.15%.
The resulting solid was further treated with cyclohexane (1000 ml) and ethanol (25 ml) at 42-48° C. The reaction mass was cooled to 25-35° C. and maintained for 1 hr, filtered, washed with cyclohexane. The resulting wet cake was suck dried initially, later dried at 25-35° C. for 2 hrs and finally dried at 47-53° C. for 8 hrs to obtain title compound as hydrochloride salt. Yield: 80 gms. HPLC Purity: 99.8%; acid-amine impurity of Formula A: less than 0.1%.

Example 2

Preparation of Sacubitril Sodium of Formula II:
Compound of formula IV (100 g), succinic anhydride (34.5 gms) and dichloromethane (800 ml) were added into a round bottom flask at 25-35° C. and stirred for 30 mins and then cooled to 0-6° C. To the reaction mixture, Triethylamine (80 ml) was added lot wise over 3 hrs in 2 lots by maintaining the temperature below 10° C. After completion of the reaction by HPLC, dilute hydrochloric acid (35 ml in 310 ml water) was added to the above reaction mass. The temperature of the reaction mass was raised to 25-35° C. and the layers were separated. The aq layer was extracted with dichloromethane and combined the organic layers and washed with 10% sodium chloride solution. Water (30 ml) and sodium carbonate (19.8 gms) were added to the resulting product containing organic layer at 25-35° C. and stirred for 3 hrs. The temperature of the reaction mixture was raised to 38-42° C. and maintained for 6 h at the same temperature. After the completion of the reaction, the excess water was removed by azeotropic distillation and then the cooled to 30° C., filtered, washed with dichloromethane and distilled the solvent completely. The crude reaction mass was stripped off with methyl ethyl ketone (200 mL) and degassed for 30 min at 50° C. HPLC analysis revealed the content of lactam impurity of Formula C: about 1 to 1.5%; succinamide Impurity of Formula D: about 0.09%; HPLC purity: 98.62%.
Methyl ethyl ketone (500 ml) was added to the above crude material at 50-55° C. and stirred for 10-20 min. n-Heptane (1000 mL) was added to the above reaction mass at the same temperature and maintained for 6 hrs. The reaction mass was then cooled to 25-35° C., maintained for 2 hrs, filtered, washed with a mixture of MEK: n-Heptane (1:2, 75 mL). The wet material was dried initially at 25-35° C. for 2 hrs and then dried at 47-53° C. for 8 hrs to obtain sacubitril sodium as white color solid; yield-100 gms; HPLC purity 99.7%, desethyl sacubitril of Formula B: 0.02%, lactam impurity of Formula C: 0.06%, succinamide impurity of Formula D: Nil.

Example 3

Figure 9:
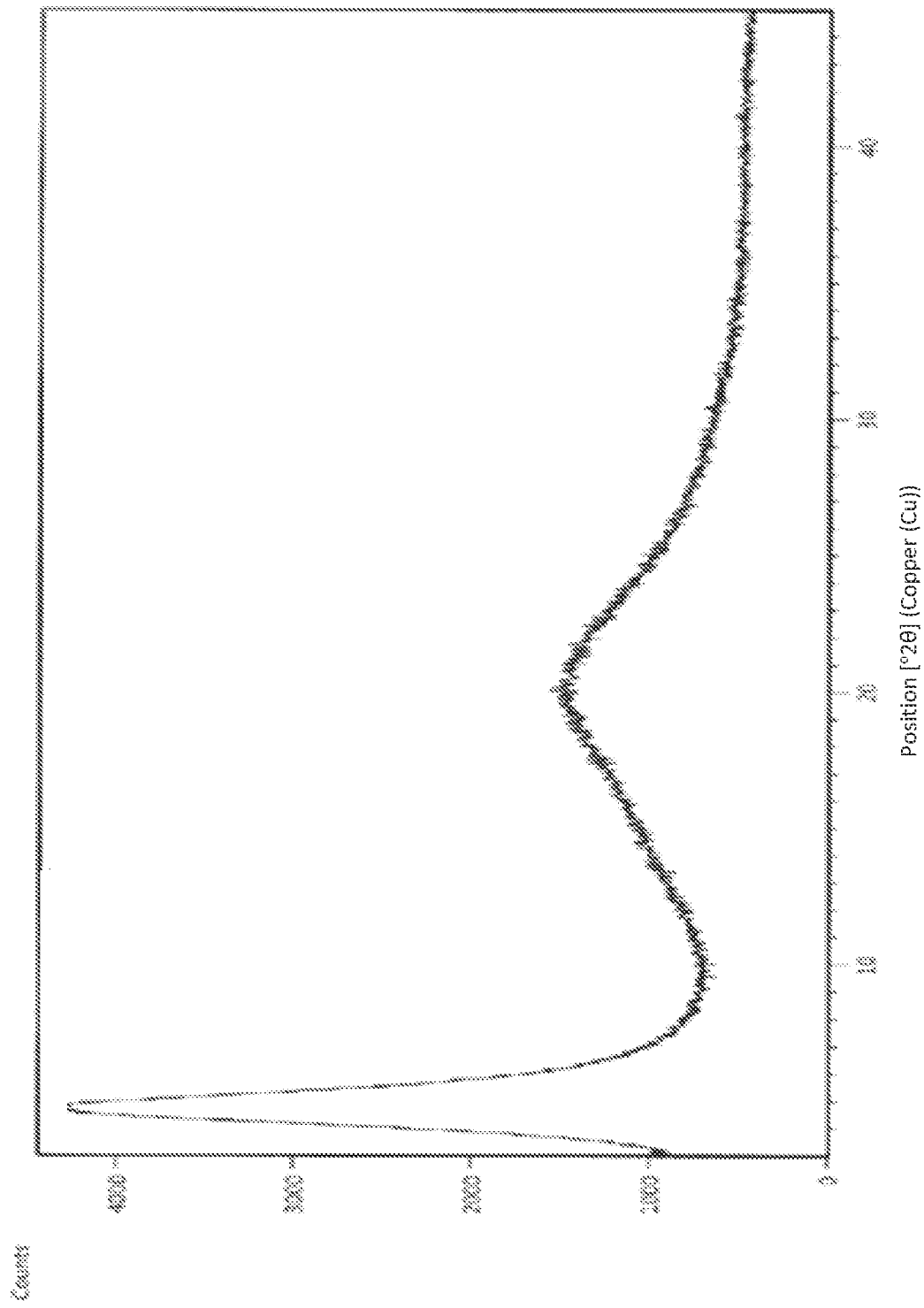
FIG. 9 is the characteristic powder X-ray diffraction (XRD) pattern of amorphous form of sacubitril valsartan trisodium complex prepared according to Example-3.

Preparation of Amorphous Form of Sacubitril Valsartan Trisodium Complex:
Ethanol (1000 ml), valsartan disodium (123.1 gms) and sacubitril sodium salt (100 gms) were added in to a round bottom flask at 25-35° C. The reaction mass was stirred for 1-2 hrs at 25-35° C. for complete dissolution. Activated carbon (5 gms) was added to the reaction mass, stirred the reaction mass for 20-30 mins, filtered and distilled the solvent completely under vacuum at below 50° C. Cyclohexane (500 ml) was added to the resulting residue, stirred for 30-60 mins, distilled the solvent completely under vacuum at below 50° C. and cooled the resulting reaction mass to 15-25° C. Cyclohexane (1000 ml) was added to the resulting reaction mass at 15-25° C., maintained for 2-3 hrs, filtered and washed with cyclohexane. The resulting wet cake was dried initially at 25-35° C. for 2 hrs, later dried at 47-53° C. for 2 hrs and finally dried at 87-93° C. for 20 hrs to obtain amorphous form. Yield: 180 gms. Desethyl sacubitril of Formula B: 0.02%, lactam impurity of Formula C: 0.02%; succinamide impurity of Formula D: Nil. The PXRD is set forth in FIG. 9.

Example 4

Preparation of Amorphous Form of Sacubitril Valsartan Trisodium Complex:

A mixture of sacubitril sodium (3 Kgs) and valsartan disodium (3.6 Kgs) were charged to the reactor and dissolved in ethanol (30 lit) at 25-35° C. The reaction mass was treated with activated carbon and stirred for 30 min at the same temperature. The reaction mass was filtered through HYFLO to remove the undissolved particulate. The clear filtrate was transferred to a cleaned reactor and distilled off the solvent completely under vacuum at below 50° C. The residue obtained was stripped off with cyclohexane and degassed for 60 min at below 50° C. The obtained solid material was cooled to 15-25° C. and cyclohexane (30 lit) was charged. The solution was stirred for 3 hrs at 15-25° C. The solid obtained was filtered and washed with cyclohexane (3 lit) and dried to provide amorphous form of sacubitril valsartan trisodium complex. Yield: 6.6 Kg.

Example 5

Preparation of Amorphous Form of Sacubitril Valsartan Trisodium Complex:

Valsartan disodium (12.3 gms) and sacubitril sodium (10 gms) were dissolved in methanol (100 ml) at 25-35° C. The resulting clear solution was filtered through HYFLO to remove any undissolved particles. The obtained filtrate was distilled off completely under vacuum at 50° C. The obtained residue was co-distilled with cyclohexane (50 ml) at below 50° C. and the resulting solid material was cooled to 20±5° C. Cyclohexane (100 ml) was added at 20±5° C. and the solution was maintained for 2 hrs at the same temperature. The solid was filtered under nitrogen atmosphere and dried at 90° C. under vacuum for 15-20 hrs to yield the amorphous form of sacubitril valsartan trisodium. Yield: 17.5 gms.

Example 6

Preparation of Amorphous Form of Sacubitril Valsartan Trisodium Complex:

A mixture of valsartan disodium (12.3 gms) and sacubitril sodium (10 gms) were dissolved in isopropyl alcohol (100 ml) under stirring, at 25-35° C. The resulting heterogeneous mass was stirred for 60 min to get a clear solution. The resulting clear solution was filtered through HYFLO at the same temperature to remove any undissolved particulate. The obtained filtrate was then concentrated under vacuum at 50° C. The obtained residue was co-distilled with cyclohexane (50 ml) at below 50° C. and degassed for 30 min. The solid residue was cooled to 20±5° C., cyclohexane (100 ml) was added and stirred the mixture at 20±5° C. for 2 hrs. The obtained solid was filtered under vacuum at 20±5° C. under $N_2$ atmosphere. The wet material was washed with cyclohexane and dried under vacuum at 90° C. for 20 hrs to obtain amorphous sacubitril valsartan complex. Yield: 15.5 gms.

Example 7

Figure 5:
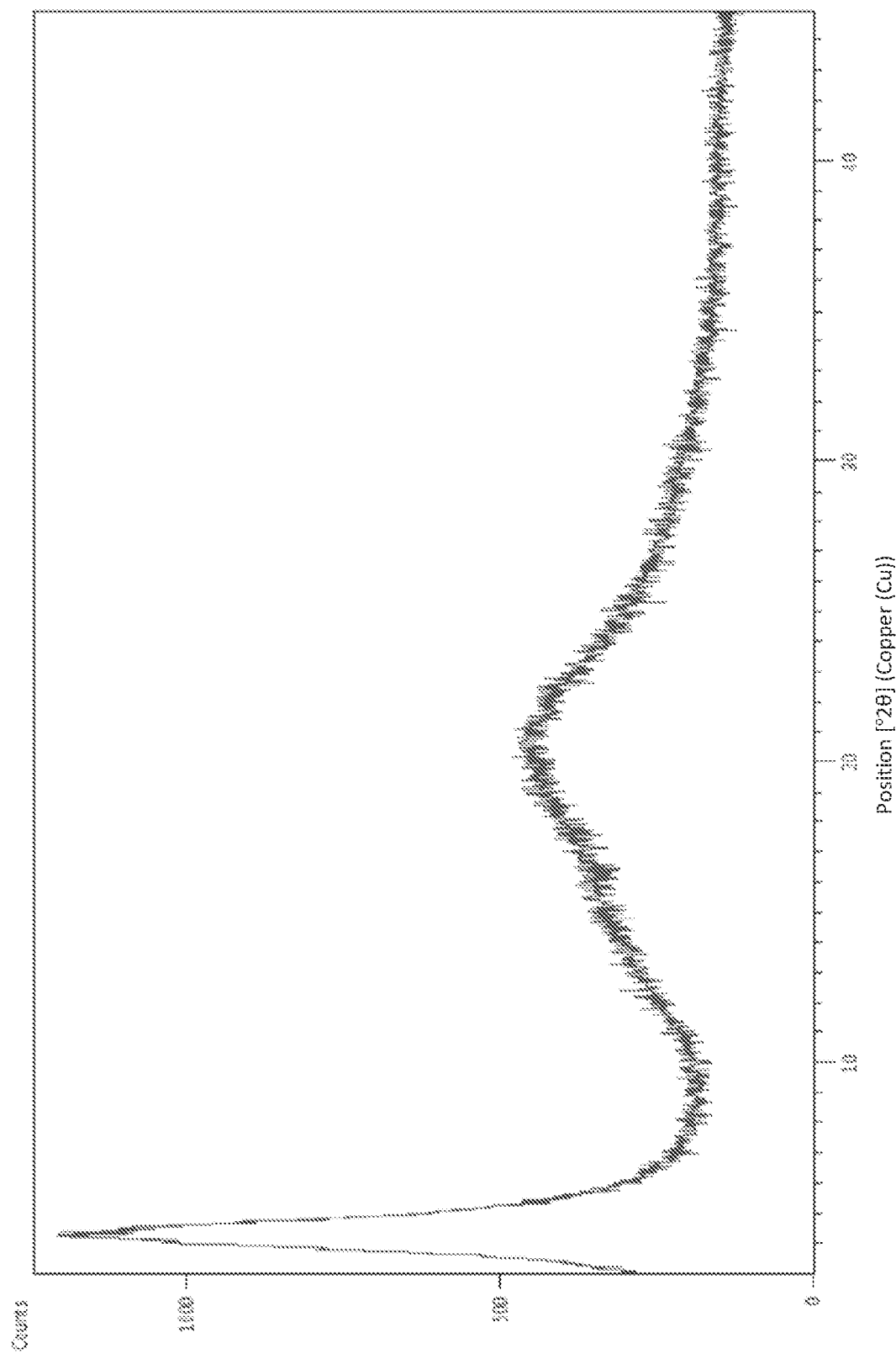
FIG. 5 is the characteristic powder X-ray diffraction (XRD) pattern of amorphous form of sacubitril valsartan trisodium complex prepared according to Example-7.

Preparation of Amorphous Form of Sacubitril Valsartan Trisodium Complex:

Acetone (100 ml), valsartan disodium (3.3 gms) and sacubitril sodium salt (3.0 gms) were added in to a round bottom flask at 25-35° C. The reaction mass was stirred for 10 min at 25-35° C. for complete dissolution, distilled out the solvent completely under vacuum at 35-40° C. and degassed the solid for 1 hr under vacuum at 35-40° C. to obtain amorphous form. Yield: 6.3 gms. The PXRD is set forth in FIG. 5.

Example 8

Preparation of Amorphous Form of Sacubitril Valsartan Trisodium Complex:

Valsartan disodium (275 mg), sacubitril sodium salt (250 mg) and acetone (10 ml) were added to a round bottom flask at 25-35° C. The resultant reaction mass was stirred at 25-35° C. for 10 mins for complete dissolution and distilled at 40° C. under vacuum. To the resulting solids, cyclohexane (5 ml) was added at 25-35° C., cooled to 10-20° C. and stirred for 3 hrs at 10-20° C. The solids were filtered under vacuum at 10-20° C. under $N_2$ atmosphere, washed with chilled cyclohexane (2 ml) and dried under vacuum at 50° C. for 16 hrs to obtain amorphous form. Yield: 356 mgs.

Example 9

Preparation of Amorphous Form of Sacubitril Valsartan Trisodium Complex:

Valsartan disodium (275 mg), sacubitril sodium salt (250 mg) and acetone (10 ml) were added to a round bottom flask at 25-35° C. The reaction mass was stirred for 10 mins at 25-35° C. for complete dissolution and distilled the solvent completely at 40° C. under vacuum. Heptane (5 ml) was added to the resulting solids at 25-35° C., cooled to 3±2° C. and stirred the mixture at 3±2° C. for 3 hrs. The obtained solids were filtered under vacuum at 3±2° C. under $N_2$ atmosphere, washed with chilled heptane (2 ml) and dried the solids under vacuum at 50° C. for 16 hrs to obtain amorphous form. Yield: 379 mgs.

Example 10

Preparation of Amorphous Form of Sacubitril Valsartan Trisodium Complex:

Crystalline Sacubitril Valsartan complex (34 gms) was dissolved in ethanol (170 ml) under stirring at 25-35° C. The reaction mass was stirred for 30 min at the same temperature and the obtained clear solution was distilled off completely at below 40° C. under vacuum. Cyclohexane (340 ml) was added to the solid and stirred for 2 h at 25-35° C. The obtained solid was filtered and the wet material was dried for 10 hrs at 50° C. under vacuum to yield amorphous sacubitril valsartan trisodium complex. Yield: 31 gms. HPLC purity: 99.96%.

Example 11

Preparation of Amorphous Solid Dispersions of Sacubitril Valsartan Trisodium Complex with Hydroxypropyl Methylcellulose (with 10% HPMC, Methanol):

Valsartan disodium (275 mg), sacubitril sodium salt (250 mg), HPMC (52 mg; 10% w/w) and methanol (20 ml) were added into a round bottom flask at 25-35° C. The resulting reaction mass was stirred for 10 mins at 25-35° C. for complete dissolution, distilled the solvent completely at 45° C. under vacuum and dried the resulting solids at 50° C. under vacuum for 16 hrs to obtain amorphous solid dispersion. Yield: 452 mgs. The PXRD is set forth in FIG. 6.

Example 12

Preparation of Amorphous Solid Dispersions of Sacubitril Valsartan Trisodium Complex with Hydroxypropyl Methylcellulose (with 20% HPMC, Methanol):

Amorphous valsartan-sacubitril sodium salt complex (200 mg), hydroxypropyl methylcellulose (50 mg; 20% w/w) and methanol (15 ml) were added into a round bottom flask at 25-35° C. The resulting reaction mass was stirred for 15 mins at 25-35° C. for complete dissolution, distilled the solvent completely at 40° C. under vacuum, degassed at 40° C. under vacuum for 1 hr and dried the resulting solids at 50° C. under vacuum for 5 hrs to obtain amorphous solid dispersion. Yield: 209 mgs. The PXRD is set forth in FIG. 7.

Example 13

Preparation of Amorphous Solid Dispersions of Sacubitril Valsartan Trisodium Complex with Hydroxypropyl Methylcellulose (with 9% HPMC, Water-Methanol):

Valsartan disodium (275 mg), sacubitril sodium salt (250 mg), HPMC (50 mg; 9% w/w), water (1 ml) and methanol (4 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 491 mgs.

Example 14

Preparation of Amorphous Solid Dispersions of Sacubitril Valsartan Trisodium Complex with Hydroxypropyl Methylcellulose (with 9% HPMC, Water-Acetone):

Valsartan disodium (275 mg), sacubitril sodium salt (250 mg), HPMC (50 mg; 9% w/w), water (1 ml) and acetone (4 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 475 mgs.

Example 15

Preparation of Amorphous Solid Dispersions of Sacubitril Valsartan Trisodium Complex with Hydroxypropyl Methylcellulose (with 19% HPMC, Water-Ethanol):

Valsartan disodium (275 mg), sacubitril sodium salt (250 mg), HPMC (125 mg; 19% w/w), water (2 ml) and ethanol (8 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 465 mgs.

Example 16

Preparation of Amorphous Solid Dispersions of Sacubitril Valsartan Trisodium Complex with Hydroxypropyl Methylcellulose (with 19% HPMC, Water-Acetone):

Valsartan disodium (275 mg), sacubitril sodium salt (250 mg), HPMC (125 mg; 19% w/w), water (2 ml) and acetone (6 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 522 mgs.

Example 17

Preparation of Amorphous Solid Dispersions of Sacubitril Valsartan Trisodium Complex with Hydroxypropyl Methylcellulose (with 26% HPMC, Water-Acetone):

Valsartan disodium (275 mg), sacubitril sodium salt (250 mg), HPMC (187.5 mg; 26% w/w), water (2 ml) and acetone (6 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 655 mgs.

Example 18

Preparation of Amorphous Solid Dispersions of Sacubitril Valsartan Trisodium Complex with Hydroxypropyl Methylcellulose (with 35% HPMC, Water-Ethanol):

Sacubitril sodium (32.4 gms) and valsartan disodium (39.6 gms) were added to ethanol (320 ml) and stirred for complete dissolution at 25-35 C. HPMC solution (8 gms dissolved in a mixture of 320 ml ethanol and 32 ml water) was added to the above reaction mass over a period of 5 min via addition flask. The temperature of the reaction mass was raised to 45° C. and stirred for 10 min at the same temperature. The obtained clear solution was distilled off under vacuum at below 50° C. The obtained glassy material was dried at 50° C. under vacuum for 12 hrs to yield amorphous sacubitril valsartan trisodium complex. Yield: 79.5 gms.

Example 19

Preparation of Amorphous Solid Dispersions of Sacubitril Valsartan Trisodium Complex with Hydroxypropyl Cellulose (with 9% HPC, Methanol):

Valsartan disodium (275 mg), sacubitril sodium salt (250 mg), HPC (50 mg; 9% w/w) and methanol (5 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 488 mgs. The PXRD is set forth in FIG. 8.

Example 20

Preparation of Amorphous Solid Dispersions of Sacubitril Valsartan Trisodium Complex with Hydroxypropyl Cellulose (with 19% HPC, Water-Acetone):

Valsartan disodium (275 mg), sacubitril sodium salt (250 mg), HPC (125 mg; 19% w/w), water (0.8 ml) and acetone (10 ml) were added into a round bottom flask at 25-35° C.

The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 463 mgs.

Example 21

Preparation of Amorphous Solid Dispersions of Sacubitril Valsartan Trisodium Complex with Hydroxypropyl Cellulose (with 26% HPC, Water-Ethanol):

Valsartan disodium (275 mg), sacubitril sodium salt (250 mg), HPC (187.5 mg; 26% w/w), water (5 ml) and ethanol (10 ml) were added into a round bottom flask at 25-35° C. The resulting reaction mass was stirred at 45-50° C. for complete dissolution, distilled the solvent completely at 45-50° C. under vacuum and dried the resulting solids at 45° C. under vacuum for 6 hrs to obtain amorphous solid dispersion. Yield: 370 mgs.

Example 22

Preparation of Amorphous Solid Dispersions of Sacubitril Valsartan Trisodium Complex with Copovidone (with 35% Copovidone, Ethanol):

Copovidone (28 gms) was dissolved in ethanol (320 ml) under stirring. The temperature of the reaction mass was raised to 45±3° C. and maintained for 10 min at the same temperature. Sacubitril sodium (23.4 gms) and valsartan disodium (28.6 gms) were added to above solution and washed the flask with ethanol (80 ml). The reaction mass was stirred for 10 min at the same temperature. The obtained clear solution was distilled off completely at below 50° C. under vacuum. The obtained solid was dried for 12 hrs at 50° C. under vacuum to yield amorphous sacubitril valsartan trisodium complex Yield: 79 gms. HPLC purity: 99.95%.

Example 23

Preparation of Amorphous Solid Dispersions of Sacubitril Valsartan Trisodium Complex with Copovidone (with 20% Copovidone, Ethanol):

Copovidone (16 gms) was dissolved in ethanol (320 ml) under stirring. The temperature of the reaction mass was raised to 45±3° C. and stirred for 10 min at the same temperature. Sacubitril sodium (28.7 gms) and valsartan disodium (35.2 gms) were added to above solution and washed with ethanol (80 ml). The reaction mass was stirred for 10 min at the same temperature. The obtained clear solution was distilled off completely at below 50° C. under vacuum. The obtained solid was dried for 12 hrs at 50° C. under vacuum to yield amorphous sacubitril valsartan trisodium complex. Yield: 79 gms. HPLC purity: 99.91%. The PXRD is set forth in FIG. 10.

Example 24

Preparation of Amorphous Solid Dispersions of Sacubitril Valsartan Trisodium Complex with Povidone (with 35% Povidone, Ethanol):

Povidone (28 gms) was dissolved in ethanol (320 ml) under stirring. The temperature of the reaction mass was raised to 45±3° C. and maintained for 10 min at the same temperature. Sacubitril sodium (23.4 gms) and valsartan disodium (28.6 gms) were added and to the reaction mass and washed with ethanol (80 ml). The reaction mass was stirred for 10 min and concentrated under vacuum at below 50° C. the solid material was dried for 12 hrs under vacuum at 50° C. to yield amorphous sacubitril valsartan complex. Yield: 79.2 gms. HPLC purity: 99.96%.

Example 25

Preparation of Amorphous Solid Dispersions of Sacubitril Valsartan Trisodium Complex with Povidone (with 20% Povidone, Ethanol):

Povidone (16 gms) was dissolved in ethanol (320 ml) under stirring. The temperature of the reaction mass was raised to 45±3° C. and maintained for 10 min at the same temperature. Sacubitril sodium (28.7 gms) and valsartan disodium (35.2 gms) were added and to the reaction mass and washed with ethanol (80 ml). The reaction mass was stirred for 10 min and concentrated under vacuum at below 50° C. The solid material was dried for 12 hrs under vacuum at 50° C. to yield amorphous sacubitril valsartan complex. Yield: 79.2 gms. HPLC purity: 99.89%. The PXRD is set forth in FIG. 11.

Example 26

Stability Study for Amorphous Trisodium Sacubitril Valsartan Complex of the Invention:

The amorphous form of trisodium sacubitril valsartan complex is packed in LDPE bag under nitrogen atmosphere and placed in another LDPE bag, filled with nitrogen and kept silica gel packet between the bags, tied with strip seal. Kept the bag in triple laminated sunlight barrier bag and sealed with heat sealer. The stability of the samples was tested at 25±2° C./60±5% RH and 40±2° C./75±5% RH respectively. The results are shown in below table 1:

TABLE 1

|  | 40 ± 2° C./75 ± 5% RH | | 25 ± 2° C./60 ± 5% RH | |
| --- | --- | --- | --- | --- |
| Time | HPLC purity (%) | PXRD | HPLC purity (%) | PXRD |
| Initial | 99.94 | Amorphous | 99.94 | Amorphous |
| 1$^{st}$ month | 99.95 | Amorphous | 99.95 | Amorphous |
| 3$^{rd}$ month | 99.93 | Amorphous | 99.94 | Amorphous |
| 6$^{th}$ month | 99.90 | Amorphous | 99.93 | Amorphous |

Figure 12:
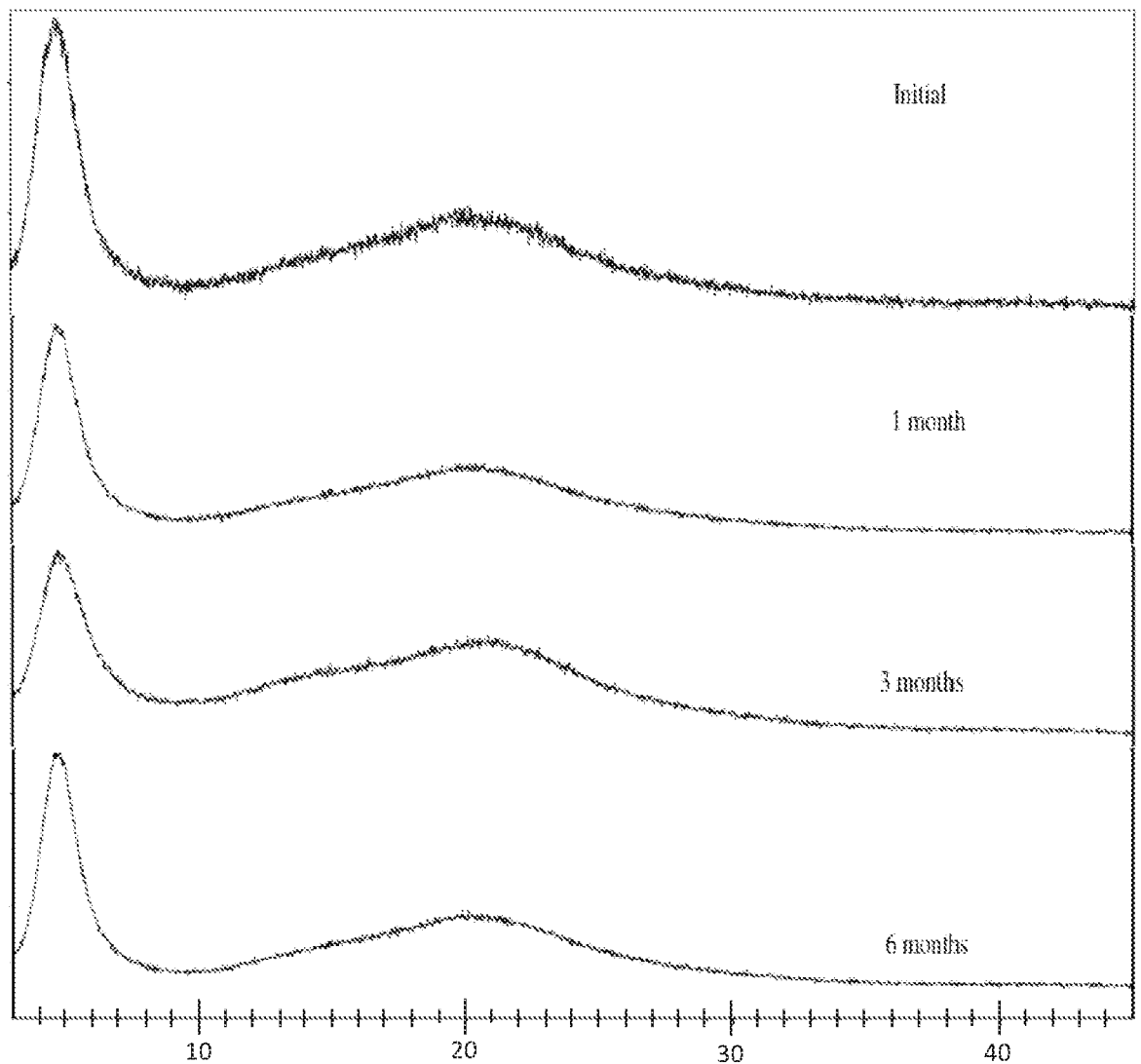
FIG. 12 is the compiling characteristic powder X-ray diffraction (XRD) pattern of amorphous form of sacubitril valsartan trisodium complex when stored at a temperature of 40±2° C. and at a relative humidity of 75±5% relative humidity (RH) for initial, 1 month, 3 months and 6 months.

FIG. 12 is the compiling characteristic powder X-ray diffraction (XRD) pattern of amorphous form of sacubitril valsartan trisodium complex when stored at a temperature of 40±2° C. and at a relative humidity of 75±5% relative humidity (RH) for initial, 1 month, 3 months and 6 months.

Example 27

Stability Study for Solid Dispersion of Amorphous Trisodium Sacubitril Valsartan Complex of the Invention:

The amorphous form of solid dispersed trisodium sacubitril valsartan complex with different pharmaceutically acceptable carriers are each separately packed in LDPE bags under nitrogen atmosphere and placed in another LDPE bag, filled with nitrogen and kept silica gel packet between the bags, tied with strip seal. Kept the bag in triple laminated sunlight barrier bag and sealed with heat sealer. The stability of the samples was tested at 25±2° C./60±5% RH and 40±2° C./75±5% RH respectively. The results are shown in below table 2:

TABLE 2

| Sample | Time | 40 ± 2° C./75 ± 5% RH | | 25 ± 2° C./60 ± 5% RH | |
|---|---|---|---|---|---|
| | | HPLC purity (%) | PXRD | HPLC purity (%) | PXRD |
| Sac + Val Amorphous complex (with 10% HPMC) | Initial 3rd month | 99.96 99.95 | Amorphous Amorphous | 99.95 99.94 | Amorphous Amorphous |
| Sac + Val Amorphous complex (with 5% HPMC) | Initial 3rd month | 99.94 99.95 | Amorphous Amorphous | 99.95 99.96 | Amorphous Amorphous |
| Sac + Val Amorphous complex (with 35% Copovidone) | Initial 3rd month | 99.96 99.96 | Amorphous Amorphous | 99.95 99.95 | Amorphous Amorphous |
| Sac + Val Amorphous complex (with 35% Povidone) | Initial 3rd month | 99.93 99.94 | Amorphous Amorphous | 99.93 99.95 | Amorphous Amorphous |
| Sac + Val Amorphous complex (with 20% Copovidone) | Initial 3rd month | 99.92 99.96 | Amorphous Amorphous | 99.92 99.94 | Amorphous Amorphous |
| Sac + Val Amorphous complex (with 20% Povidone) | Initial 3rd month | 99.91 99.94 | Amorphous Amorphous | 99.91 99.95 | Amorphous Amorphous |

It will be understood that various modifications may be made to the embodiments disclosed herein. Therefore the above description should not be constructed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparation of sacubitril sodium salt of Formula II,

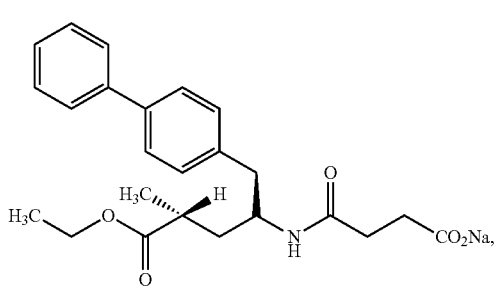

Formula II comprising:

a) reacting a compound of Formula III with a suitable halogen source in presence of ethanol and a suitable non-polar solvent to obtain a compound of Formula IV or its acid addition salt thereof,

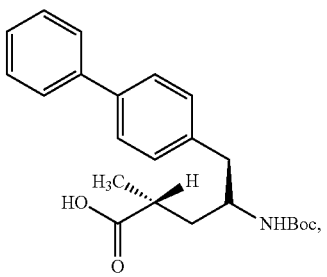

Formula III

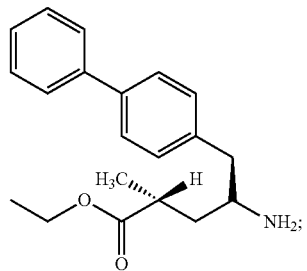

Formula IV b) treating the compound of Formula IV or its acid addition salt with succinic anhydride in presence of a base to obtain sacubitril of Formula V,

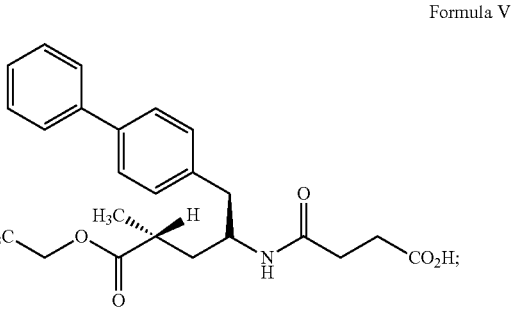

Formula V and c) treating the sacubitril of Formula V with a suitable sodium source to obtain the sacubitril sodium of Formula II.

2. The process of claim 1, wherein the suitable halogen source is selected from the group consisting of thionyl chloride, oxalyl chloride, phosgene or acetyl chloride.

3. The process of claim 1, wherein the suitable non-polar solvent is selected from the group consisting of cyclohexane, heptane, hexane, dichloromethane, toluene; and mixtures thereof.

4. The process of claim 1, wherein the step a) reaction is carried out with thionyl chloride in presence of ethanol and cyclohexane.

5. The process of claim 1, wherein base is selected from the group consisting of diethylamine, triethylamine, diisopropylamine, diisopropylethylamine, pyridine, piperidine, morpholine or DBU.

6. The process of claim 1, wherein the base is added in a lot wise manner.

7. The process of claim 1, wherein the step b) is carried out in a solvent selected from the group consisting of dichloromethane, dimethylformamide, dimethylacetamide, dimethylsulfoxide, N-methylpyrrolidone, acetonitrile, tetrahydrofuran or 2-methyltetrahydrofuran.

8. The process of claim 1, wherein the sodium source is selected from the group consisting of sodium carbonate, sodium bicarbonate or sodium 2-ethyl hexanoate.

9. The process of claim 1, further comprising:

d) purifying the sacubitril sodium of Formula II obtained in step c), comprising:

i) dissolving sacubitril sodium salt of Formula II in one or more solvents;

ii) optionally adding an antisolvent to the step i) reaction mixture or vice-versa; and iii) isolating the pure sacubitril sodium salt of Formula II.

10. The process of claim 9, wherein the one or more solvents are selected from ketones, esters, halogenated hydrocarbons and mixtures thereof.

11. The process of claim 10, wherein the one or more solvents are selected from the group consisting of acetone, methyl isobutyl ketone, methyl ethyl ketone, methyl acetate, ethyl acetate, isopropyl acetate, n-propyl acetate, n-butyl acetate, t-butyl acetate, dichloromethane, dichloroethane, chloroform and mixtures thereof.

12. The process of claim 9, further comprises adding an antisolvent to the step i) solution selected from the group consisting of toluene, xylene, n-hexane, n-heptane, cyclohexane, cycloheptane, tetrahydrofuran, dimethyl ether, diisopropyl ether, methyl tertiary butyl ether, 1,4-dioxane and mixtures thereof.

13. The process of claim 9, wherein the solvent of step i) is methyl ethyl ketone and the anti solvent of step ii) is n-heptane.

14. The process of claim 1, further comprising:

preparing a pharmaceutical composition by combining the sacubitril sodium of Formula II with at least one pharmaceutically acceptable excipient.

* * * * *